United States Patent [19]

Nakane

[11] Patent Number: 4,595,692
[45] Date of Patent: Jun. 17, 1986

[54] 7-THIABICYCLOHEPTANE SUBSTITUTED ETHERS

[75] Inventor: Masami Nakane, Hopewell, N.J.

[73] Assignee: E. R. Squibb & Sons, Inc., Princeton, N.J.

[21] Appl. No.: 735,250

[22] Filed: May 17, 1985

[51] Int. Cl.[4] ............... A61K 31/38; C07D 333/64; C07D 333/56
[52] U.S. Cl. .................... 514/443; 549/53; 549/58
[58] Field of Search ............... 549/58, 53; 514/443

[56] References Cited

U.S. PATENT DOCUMENTS

| | | |
|---|---|---|
| 4,143,054 | 3/1979 | Sprague . |
| 4,187,236 | 2/1980 | Sprague . |
| 4,220,594 | 9/1980 | Sprague . |
| 4,228,180 | 10/1980 | Sprague . |
| 4,254,044 | 3/1981 | Sprague . |
| 4,367,237 | 1/1983 | Wakatsuka et al. ............ 549/58 |
| 4,474,803 | 10/1984 | Hall et al. . |

FOREIGN PATENT DOCUMENTS 0043292 8/1982 European Pat. Off. .
2039909 8/1980 United Kingdom .

*Primary Examiner*—Alan Siegel
*Attorney, Agent, or Firm*—Lawrence S. Levinson; Burton Rodney

[57] ABSTRACT

Bicycloheptane substituted ether prostaglandin analogs are provided having the structural formula

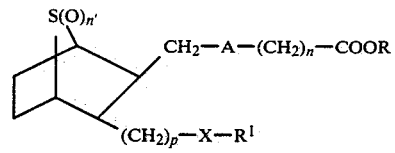

wherein X is O or

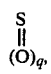

and including all stereoisomers thereof.

The compounds are cardiovascular agents useful, for example, in the treatment of thrombotic disease.

20 Claims, No Drawings

7-THIABICYCLOHEPTANE SUBSTITUTED ETHERS

DESCRIPTION OF THE INVENTION

The present invention relates to thiabicycloheptane substituted ether prostaglandin analogs which are cardiovascular agents useful, for example, in the treatment of thrombotic disease. These compounds have the structural formula

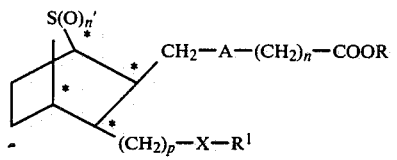

and including all stereoisomers thereof, wherein A is —CH=CH— or —(CH$_2$)$_2$, n is 0 to 8, n' is 0 or 1, p is 1 to 4, X is O or

wherein q is 0, 1 or 2; R is H, lower alkyl, alkali metal or a polyhydroxylamine salt such as tris(hydroxymethyl)amino methane or glucamine, and R$^1$ is lower alkyl, aryl, aralkyl, cycloalkyl, cycloalkylalkyl, lower alkenyl or lower alkynyl.

Thus, the compounds of the invention include the following types of compounds:

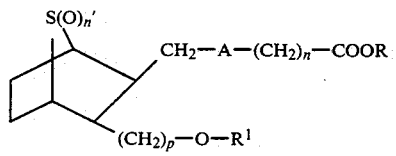
IA

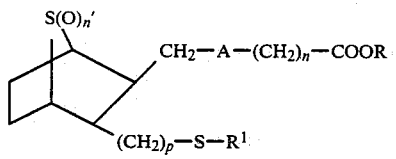
IB

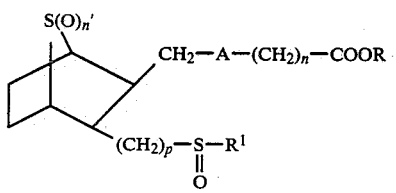
IC

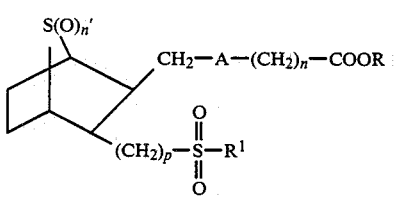
ID

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups substituted with halo, such as F, Br, Cl or I or CF$_3$; hydroxy, alkylamino; alkanoylamino; arylcarbonylamino; nitro; cyano; thiol; alkylthiol; alkoxy; aryl; alkyl-aryl; haloaryl; cycloalkyl; or alkylcycloalkyl.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups; lower alkoxy groups; 1 or 2 hydroxyl groups; 1 or 2 alkylamino groups; 1 or 2 alkanoylamino groups; 1 or 2 arylcarbonylamino groups; 1 or 2 amino groups; 1 or 2 nitro groups; 1 or 2 cyano groups; 1 or 2 thiol groups; and/or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituted on either the phenyl or naphthyl may be 1 or 2 lower alkyl groups, 1 or 2 aryl groups, 1 or 2 halogens (Cl, Br or F); 1 or 2 hydroxy groups; 1 or 2 lower alkoxy groups; 1 or 2 nitro groups; 1 or 2 cyano groups; 1 or 2 thiol groups; and/or 1 or 2 alkylthio groups. In addition, the aryl group may be substituted with 1 or 2 NR$^2$R$^3$ groups or 1 or 2

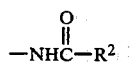

groups, wherein R$^2$ and R$^3$ are the same or different and can be hydrogen, lower alkyl or aryl.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term "halogen" or "halo" as used herein by itself or as part of another group refers to chlorine, bromine, fluorine or iodine, with chlorine being preferred.

The terms "(CH$_2$)$_n$" and "(CH$_2$)$_p$" include a straight or branched chain radical having 1 to 8 carbons in the normal chain in the case of "(CH$_2$)$_n$" and 1 to 5 carbons in the normal chain in the case of "(CH$_2$)$_p$" and may contain one or more lower alkyl and/or halo substituents. Examples of $(CH_2)_n$ and $(CH_2)_p$ groups include

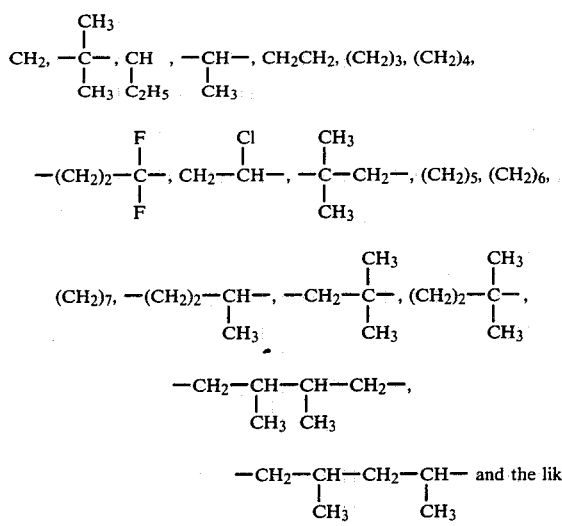

Preferred are those compounds of formula I wherein A is —CH=CH— or —CH$_2$—CH$_2$—, n is 2 to 4, p is 1, X is O or S, R is H, and R$^1$ is lower alkyl, such as hexyl, aryl, such as phenyl, or aralkyl such as benzyl.

The various compounds of the invention may be prepared as outlined below.

The 7-thiabicycloheptane ether compounds of formula I of the invention wherein X is O, p is 1, A is CH=CH or CH$_2$—CH$_2$, and n is 0 to 8, that is,

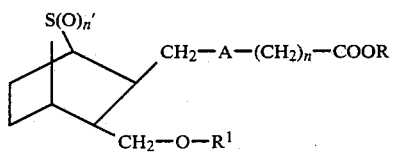

may be prepared starting with the acetal II

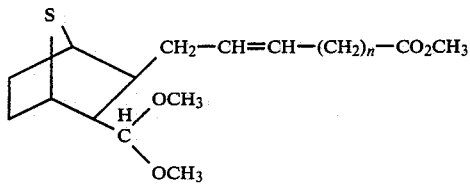

which is treated with an acid, such as trifluoroacetic acid, p-toluenesulfonic acid or hydrochloric acid in the presence of formaline and acetone to form the aldehyde IIA

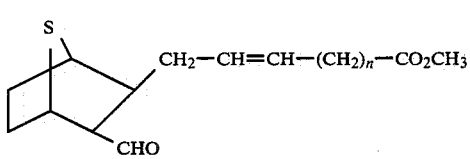

which is treated with reducing agent such as sodium borohydride in the presence of a solvent such as methanol at reduced temperatures to form alcohol IIB

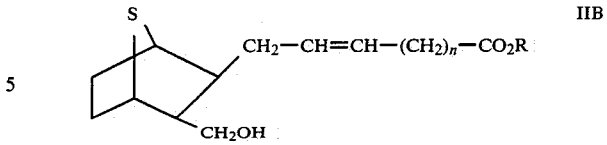

(where R is lower alkyl)

Alcohol IIB is subjected to an ether formation reaction wherein compound IIB is reacted with a strong base such as KOH, NaOH or LiOH and the like in the presence of an inert solvent, such as xylene, toluene, benzene or mesitylene and then after partial removal of solvent, reacting with a sulfonate compound of the structure Z Mesyl-OR$^1$ or
Z′ Tosyl-OR$^1$ or a halide of the structure
Z″ R$^1$X (X is Cl or Br) to form the ether

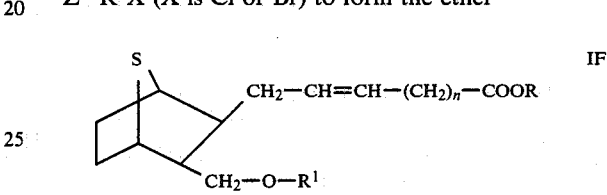

Ether IF is then hydrolyzed by treating with strong base such as LiOH, KOH or NaOH to form the corresponding alkali metal salt and then neutralizing with a strong acid such as HCl or oxalic acid to form IG

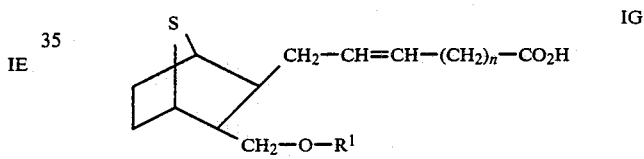

Compounds of the invention wherein X is O, A is CH$_2$—CH$_2$ and n is 0 to 8 may be prepared by subjecting acid IG to hydrogenation by treating IG with hydrogen in the presence of a catalyst such as palladium on carbon and inert solvent such as tetrahydrofuran or ethyl acetate to form acid IH

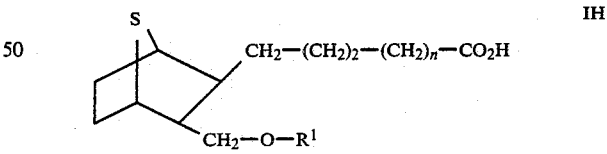

Compounds of formula I wherein X is S, A is CH=CH, p is 1 may be prepared by starting with the hydroxymethyl compound IIB

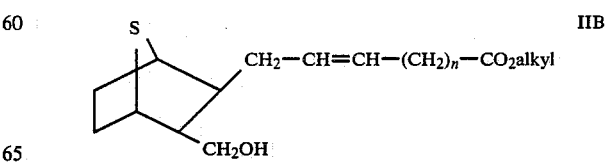

and subjecting IIB to a tosylation reaction, for example, by reacting the hydroxymethyl compound with tosyl chloride in pyridine and methylene chloride to form the corresponding tosylate III

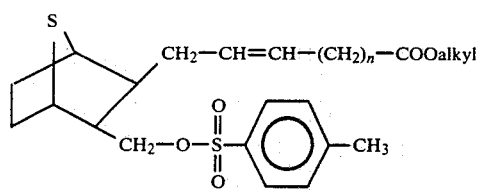  III

Thereafter, tosylate III is reacted with a thiol or mercaptan of the structure Y

HSR$^1$  Y in the presence of potassium t-butoxide and a solvent such as tetrahydrofuran, dimethyl sulfoxide or dimethylformamide to form compounds of the invention of the structure IV

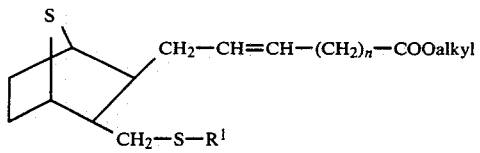  IV

Ester IV may then be hydrolyzed by treating with strong alkali metal base and then neutralizing with a strong acid, as described hereinbefore, to form the acid

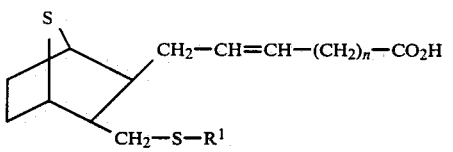  IJ

Compounds of the invention wherein p is 1, X is S, A is $CH_2$—$CH_2$ and n is 0 to 8 may be prepared by subjecting the hydroxymethyl compound IIB to hydrogenation by treating IIB with hydrogen in the presence of a catalyst such as palladium and an inert solvent such as tetrahydrofuran to form hydroxymethyl compound IIC

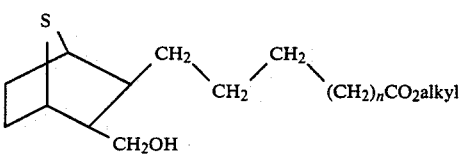  IIC

Compound IIC is then subjected to a tosylation reaction, for example, by reacting the hydroxymethyl compound with tosyl chloride in pyridine and methylene chloride to form the corresponding tosylate IIIA

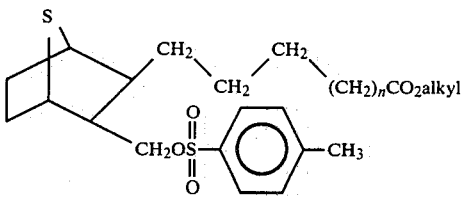  IIIA

Thereafter, tosylate IIIA is reacted with a thiol or mercaptan of the structure B, above, in the presence of potassium t-butoxide and a solvent, such as tetrahydrofuran, dimethylsulfoxide, or dimethylformamide to form compounds of the invention of structure IVA

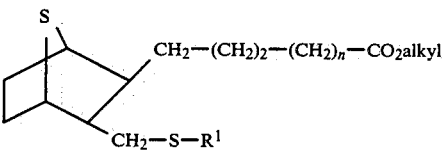  IVA

Ester IVA may then be hydrolyzed by treating with strong alkali metal base and then neutralizing with a strong acid as described hereinbefore to form the acid IK

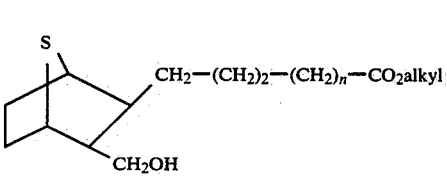  IK

Compounds of formula I wherein p is 2 to 4 may be prepared by subjecting hydroxymethyl compound II wherein A is CH=CH or hydroxymethyl compound IIC wherein A is —$(CH_2)_2$—

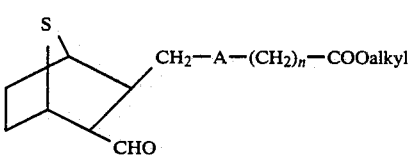  IIC (formed by reducing II by treating with hydrogen in the presence of a palladium on carbon catalyst) to a Collins oxidation by reacting II or IIA with chromium trioxide in the presence of a basic solvent such as pyridine and dichloromethane to form aldehyde V. Aldehyde V S
|
CH$_2$—A—(CH$_2$)$_n$—COOalkyl
CHO
V wherein A is CH+CH or $CH_2$—$CH_2$ is subjected to a homologation sequence, such as a Wittig reaction with $(C_6H_5)_3P$=CHOCH$_3$ followed by hydrolysis, p times, to form aldehyde VI

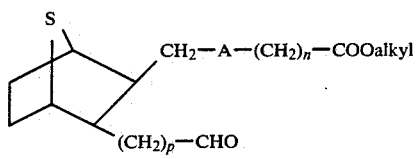

which is carried on to compounds of the invention where p is 1 to 3 by reducing aldehyde VI employing a reducing agent such as sodium borohydride in a solvent such as methanol to form alcohol ester VII

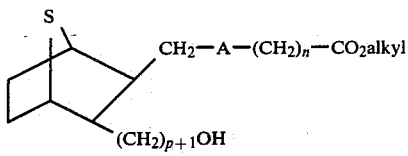

which is subjected to an etherification reaction with Z, Z' or Z" as described above or to a thioetherification reaction with thiol Y after conversion of VII to its tosylate VIIA to form VIII

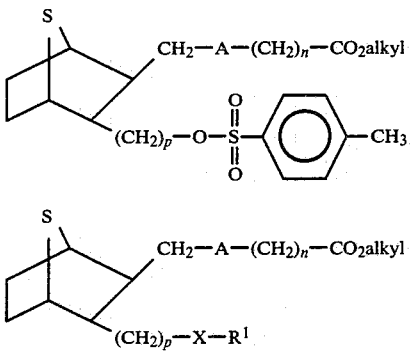

which may be hydrolyzed to the corresponding acid VIIA as described hereinbefore with respect to the conversion of ester IF to acid IG

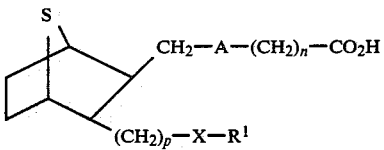

Compounds of formula I of the invention wherein X is O and $S(O)_{n'}$ is SO, that is

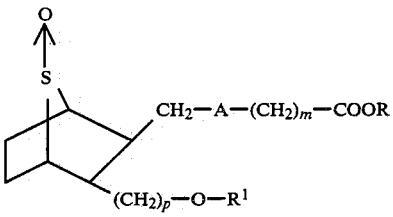

may be prepared by reacting an acid compound of formula IG or IH or VIIIA (where X is O) wherein n' is 0 and R is H with sodium periodate or other oxidizing agent such as hydrogen peroxide, or m-chloroperbenzoic acid, in methanol-water, at reduced temperatures of from about 0° C. to about 30° C. and preferably at about 20° C.

Compounds of formula I of the invention wherein X is S and $S(O)_{n'}$ is SO, that is

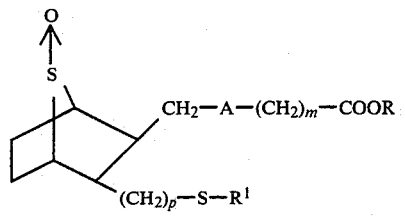

may be prepared by reacting tosylate III or IIIA or the tosylate VIIA wherein n' is 0 with sodium periodate or other oxidizing agent such as hydrogen peroxide, or m-chloroperbenzoic acid, in methanol-water, at reduced temperatures of from about 0° C. to about 30° C. and preferably at about 20° C. to form sulfoxide IX

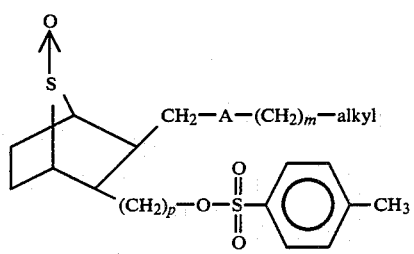

which is then subjected to thioetherification by reaction with thiol Y to form ester sulfoxide IN

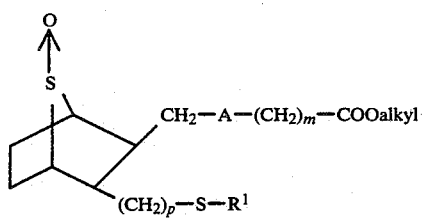

which may then be hydrolyzed as described above to form the acid IO

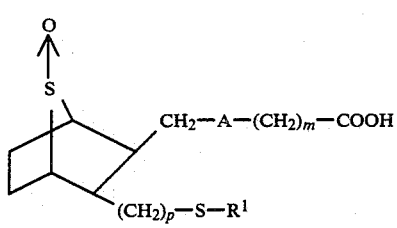

The starting hydroxymethyl compound II may be prepared according to the following reaction sequences.

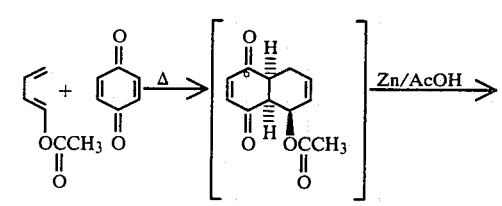
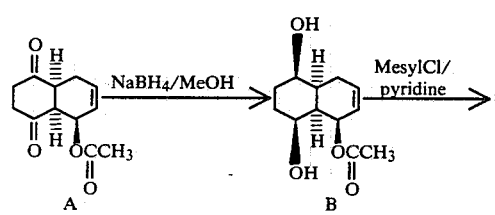
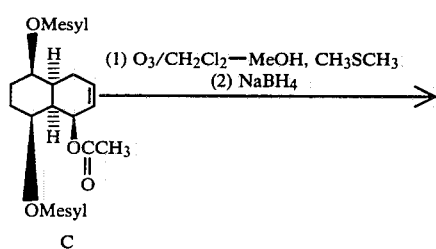
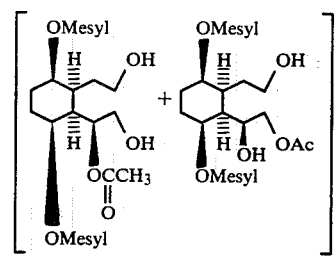
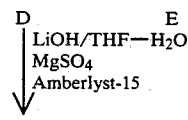
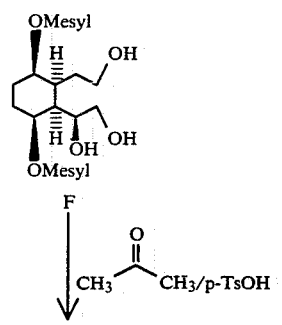
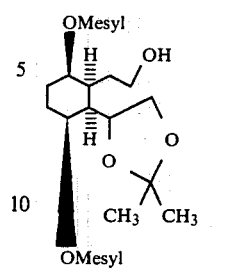
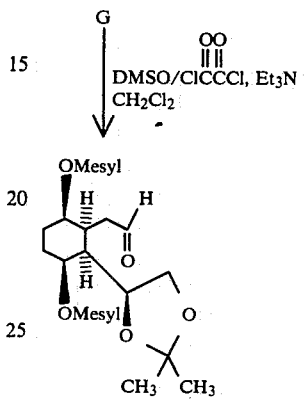
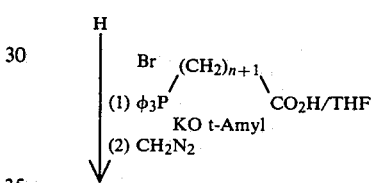
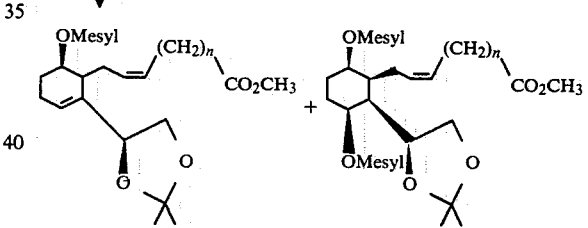
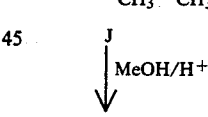
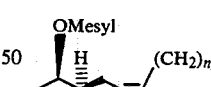
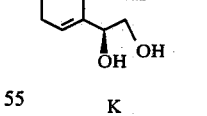
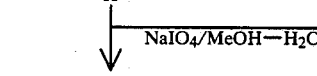
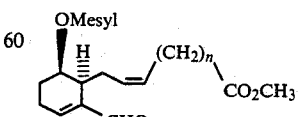
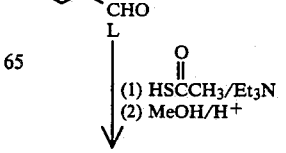

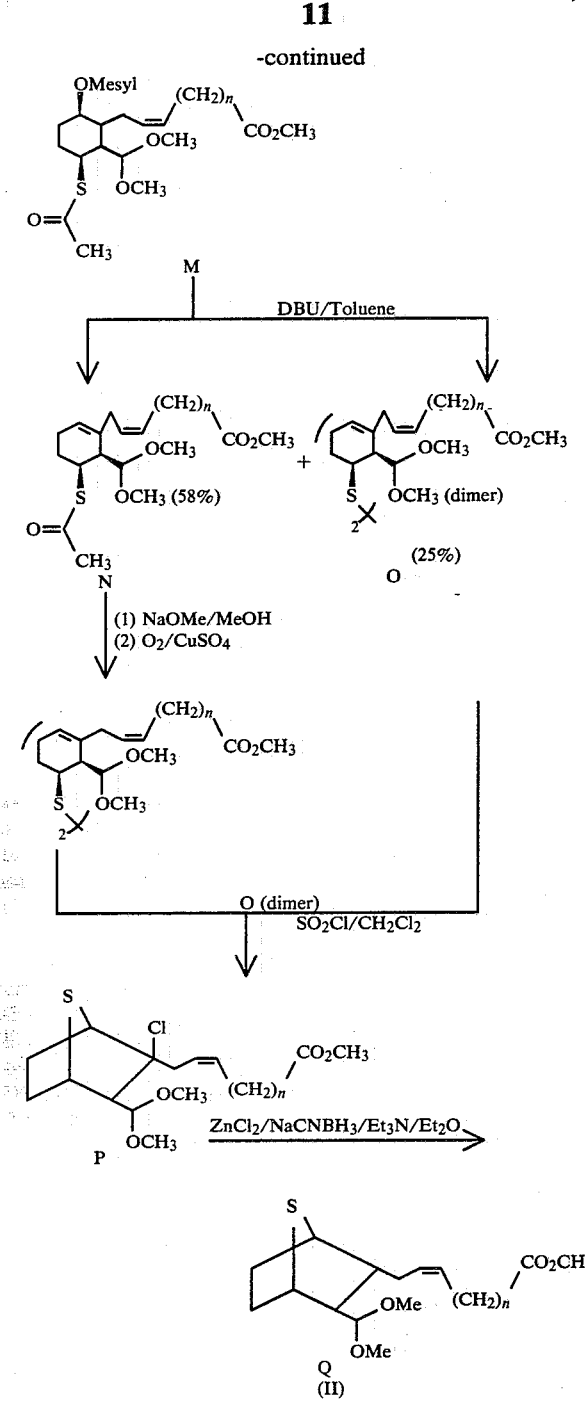

To form compounds of formula I wherein X is $$\overset{O}{\underset{O}{\overset{\|}{\underset{\|}{S}}}} \text{ and } \overset{O}{\underset{O}{\overset{\|}{\underset{\|}{S}}}},$$

the sulfide derivative of formula I wherein X is S is subjected to an oxidation reaction, for example, by reacting same with sodium periodate, in the presence of methanol and tetrahydrofuran, to form the corresponding sulfoxide derivative $$\overset{(S)}{\overset{\|}{O}}$$

and sulfonyl derivative $$\overset{O}{\underset{O}{\overset{\|}{\underset{\|}{(S)}}}}.$$

The sulfoxide and sulfonyl derivatives may be separated by chromatography or other conventional separation procedures.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

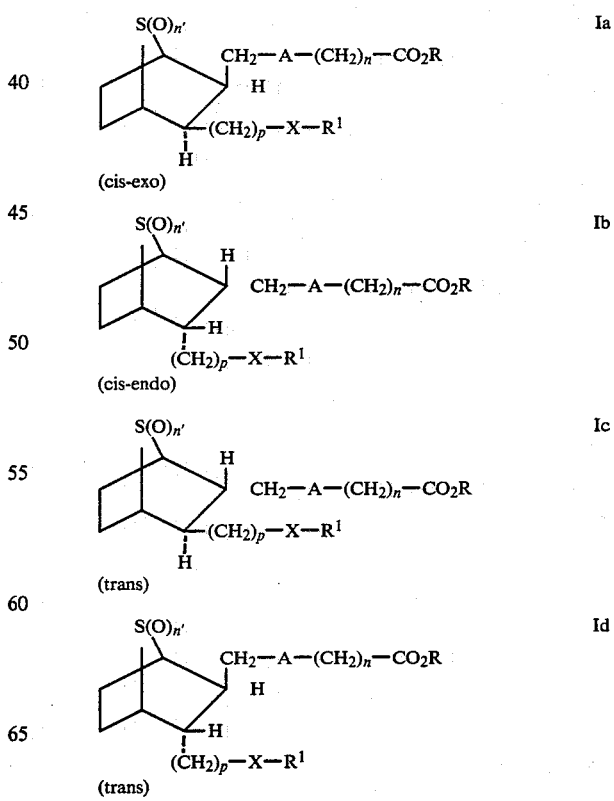

The nucleus in each of the compounds of the invention is depicted as

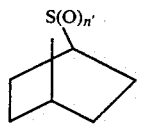

for matter of convenience; it will also be appreciated that the nucleus in the compounds of the invention may be depicted as

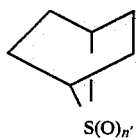

The compounds of this invention are cardiovascular agents useful as platelet aggregation inhibitors, such as inhibiting arachiodonic acid-induced platelet aggregation (e.g., for treatment of thrombotic disease, such as inhibiting coronary or cerebral thromboses) and in inhibiting bronchoconstriction as induced by asthma. They are also selective thromboxane $A_2$ receptor antagonists, e.g., having a vasodilatory effect for treatment of myocardial ischemic disease, such as angina pectoris.

The compounds of the invention are also thromboxane synthetase inhibitors and thus may also be used for preventing gastrointestinal ulcer formation. They also increase the amount of endogenous prostacyclin $PGD_2$ and therefore may be used for controlling tumor cell metastasis or as antihypertensive agents.

The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp. Ther. 141:369, 1963]. They may be used to decrease joint swelling tenderness, pain and stiffness in conditions such as rheumatoid arthritis.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1α,2β(Z),3β,4α]-7-[3-[(Hexyloxy)methyl]-7-thiabicyclo[2.2.1]hept-2-yl]-5-heptenoic acid, hexyl ester

A.

(4aα,5β,8aα)-5-(Acetyloxy)-1,2,3,4,4a,5,8,8a-octahydro-1,4-naphthalenedione

1-Acetoxy-1,3-butadiene (150 g, 1.338 mole) was added to p-quinone (131 g, 1.213 mole) in $CCl_4$ (100 ml) and diisopropyl ether (350 ml). The reaction was heated in a steam bath with occasional swirling, until the reaction became homogeneous. The reaction was allowed to cool to 35° C. The reaction was then heated at reflux for one hour and concentraed in vacuo. Zn dust (200 g) was added portionwise to a mechanically stirred solution of the resulting straw-colored oil in $Et_2O$ (100 ml) and glacial AcOH (500 ml) at 5°~10° C. The reaction was kept below 20° C. Stirring was continued for one hour at 5°~15° C. EtOAc (500 ml) was added to the reaction, which was filtered. The filter cake was washed with EtOAc (~800 ml). The filtrate was concentrated below 30° C. in vacuo to remove most of the acetic acid. The residue was dissolved in EtOAc (600 ml) and combined with the wash, which was washed with saturated $NaHCO_3$ (100 ml) and brine (200 ml×2). $NaHCO_3$ and brine washes were combined and re-extracted with EtOAc (400 ml). The EtOAc re-extract was washed with brine (100 ml×2). All the EtOAc layers were combined and dried over $MgSO_4$. Filtration and evaporation of solvent gave a straw-colored sludge. Diisopropyl ether (120 ml) was added and filtered. The resulting white powdery solids were washed again with diisopropyl ether (100 ml). The white solids (192 g) obtained were recrystallized from isopropyl alcohol (384 ml) to afford colorless crystals (178 g). The mother liquor and the diisopropyl ether washes were combined and crystallized in the same way to give additional crystals (30 g). Thus, the desired title compound (208 g, 0.937 mole, 77% from p-quinone) was obtained.

Cf J.O.C. (1964) 1341-1348, I. A. Kaye and R. S. Matthews.

B.

(1α,4α,4aβ,5α,8aβ)-1,2,3,4,4a,5,8,8a-Octahydro-1,4,5-naphthalenetriol, 5-acetate Part A compound (146 g, 0.657 mole) was dissolved in MeOH (1000 ml) and $CH_2Cl_2$ (500 ml). The reaction was cooled to −30° C.~−35° C. $NaBH_4$ (18.3 g, 0.495 mole) was added in portions under mechanical stirring. Stirring was continued for 2 hours at −30° C.~−35° C. after completion of the addition. The reaction was gradually warmed to −15° C. Then, $NH_4Cl$ solution ($NH_4Cl$, 35 g in $H_2O$, 150 ml) was added. The reaction was vigorously stirred for 30 minutes at −15° C. and concentrated in vacuo to ~400 ml. Brine (100 ml) and saturated $NH_4Cl$ (50 ml) was added to the residue. The products were extracted with EtOAc (1500 ml, 300 ml×2). The combined EtOAc layers were washed with brine (150 ml) and dried over $Na_2SO_4$. Filtration and evaporation of solvents gave a pale yellow oil (161 g), which was redissolved in MeOH (~300 ml) and concentrated to remove a possible impurity of boric acid. The resulting pale yellow oil (158 g) upon heating in diisopropyl ether (800 ml) under vigorous agitation, solidified. The solids were harvested, washed with diisopropyl ether (100 ml) to give white solids (116 g). The mother liquor and the wash were combined, and concentrated in vacuo to ~400 ml. Colorless crystals (8.9 g) were obtained from the concentrate. Thus, the desired title diol compound (124.9, 0.553 mole, 84%) was obtained.

Cf J.O.C. (1964) 1341–1348. I. A. Kaye and R. S. Matthews.

C.
(1α,4α,4aβ,5α,8aβ)-1,2,3,4,4a,5,8,8a-Octahydro-1,4,5-naphthalenetriol, 5-acetyl-1,4-bis(methanesulfonate)

Part B diol (50 g, 0.221 mole) was suspended in pyridine (250 ml) and cooled to 0° C. Mesyl chloride (50 ml, 0.646 mole) was added dropwise. Stirring was continued at 0° C. for one hour. The reaction was gradually warmed to room temperature and left overnight. The reaction was poured into ice (~500 ml) and stirred for one hour. The resulting white precipitate was harvested and washed with water until the wash became neutral NH$_4$Cl (50 ml) were added to the residue. The products were extracted with EtOAc (1500 ml, 300 ml×2). The combined EtOAc layers were washed with brine (150 ml) and dried over Na$_2$SO$_4$. Filtration and evaporation of solvents gave a pale yellow oil (161 g), which was redissolved in MeOH (~300 ml) and concentrated to remove a possible impurity of boric acid. The resulting pale yellow oil (158 g) upon heating in diisopropyl ether (800 ml) under vigorous agitation, solidified. The solids were harvested, washed with diisopropyl ether (100 ml) to give white solids (116 g). The mother liquor and the wash were combined, and concentrated in vacuo to ~400 ml. Colorless crystals (8.9 g) were obtained from the concentrate. Thus, the desired title diol compound (124.9, 0.553 mole, 84%) was obtained.

Cf J.O.C. (1964) 1341–1348. I. A. Kaye and R. S. Matthews.

C.
(1α,4α,4aβ,5α,8aβ)-1,2,3,4,4a,5,8,8a-Octahydro-1,4,5-naphthalenetriol, 5-acetyl-1,4-bis(methanesulfonate)

Part B diol (50 g, 0.221 mole) was suspended in pyridine (250 ml) and cooled to 0° C. Mesyl chloride (50 ml, 0.646 mole) was added dropwise. Stirring was continued at 0° C. for one hour. The reaction was gradually warmed to room temperature and left overnight. The reaction was poured into ice (~500 ml) and stirred for one hour. The resulting white precipitate was harvested and washed with water until the wash became neutral (~pH 5). The white solids were dried in a heated vacuum oven at 40° C.-50° C. The desired title dimesylate product (75 g, 0.196 mole, 88%) was obtained.

Cf J.O.C. (1964) 1341–1348, I. A. Kaye and R. S. Matthews.

D, E, and F.
(1α,2β,3β,4α)-2-[(S*)-1,2-Dihydroxyethyl]-3-(2-hydroxyethyl)-1,4-cyclohexanediol, 1,4-bis(methanesulfonate)(F)

Part C dimesylate (72 g, 0.188 mole) was dissolved in CH$_2$Cl$_2$ (540 ml) and MeOH (208 ml). After the solution was cooled to −78° C., O$_3$ was introduced until the reaction became blue. An excess of O$_3$ was purged with a stream of O$_2$ for 20 minutes, followed by N$_2$ for 30 minutes. Dimethyl sulfide (29.2 ml) was added and the reaction was warmed to −30° C. gradually. Additional MeOH (400 ml) was added and the reaction was stirred for 30 minutes at −30° C. Then NaBH$_4$ (14.8 g, 0.4 mole) was added portionwise over 20 minutes. The reaction was gradually warmed to −10° C. and stirred for one hour. NH$_4$Cl (53 g) in H$_2$O (150 ml) was added and the reaction was concentrated in vacuo to ~300 ml. Brine (100 ml) was added to the residue, which was extracted with EtOAC (800 ml, 400 ml×3). The combined EtOAc layers were dried over MgSO$_4$. Filtration and evaporation of solvents gave a colorless heavy oil (95 g). MeOH (300 ml) was added to the oil and the resulting homogeneous solution was concentrated to dryness to remove a possible impurity of boric acid. A pale yellow oil (81 g, a mixture of secondary acetate (D) and primary acetate (E)) was obtained. LiOH.H$_2$O (15.8 g) dissolved in H$_2$O (100 ml) was added to the oil (81 g) dissolved in THF (1300 ml). The reaction was mechanically stirred for 4 hours at room temperature. MgSO$_4$ (solid, 75 g) was added and the reaction was filtered. The filter cake was washed with THF (300 ml). The filtrate and the washes were combined and treated with Amberlyst-15 resin (35 g). The reaction was stirred for 5 minutes and filtered through Celite, which was washed with THF (200 ml). The filtrate and the washes were combined and concentrated in vacuo to give a viscous oil (61.5 g), which partially solidified upon standing in a cold room. The resulting solid title triol was crystallized from isopropanol (210 ml) to give white solids (59.68 g, 0.159 mole, 84% from Part C dimesylate).

Anal Calcd for C$_{12}$H$_{24}$O$_9$S$_2$: C, 38.28; H, 6.42; S, 17.03. Found: C, 38.31, H, 6.46; S, 16.97.

G.
(1α,2β,3β,4α)-2-[(S*)-2,2-Dimethyl-1,3-dioxolan-4-yl]-3-(2-hydroxyethyl)-1,4-cyclohexanediol, 1,4-bis(methanesulfonate)

p-TosylOH.H$_2$O (260 mg, 0.00126 mole) was added to a magnetically stirred suspension of Part F triol (61 g, 0.162 mole) in acetone (1600 ml, dried over B$_2$O$_3$). The reaction became homogeneous in 30 minutes and stirring was continued overnight. 3A molecular sieve (30 g) was added and the reaction was stirred for an additional 2.5 hours. Then, NaHCO$_3$ (1.1 g, 0.0131 mole) in H$_2$O (15 ml) was added. The reaction was filtered through a Celite pad, and concentrated in vacuo to give white solids (69 g). Slow addition of diisopropyl ether to the solids dissolved in hot acetone (100 ml) gave the title alcohol in the form of a white fine powder (65.5 g, 0.157 mole, 97%).

Anal Calcd for C$_{15}$H$_{28}$O$_9$S$_2$: C, 43.25; H, 6.77; S, 15.39. Found: C, 43.35; H, 6.84; S, 15.35.

H.
(1α,2α,3β,6β)-2-[(S*)-2,2-Dimethyl-1,3-dioxolan-4-yl]-3,6-bis[(methylsulfonyl)oxy]cyclohexaneacetaldehyde DMSO (5.08 ml) in CH$_2$Cl$_2$ (30 ml) was added dropwise to oxalyl chloride (2.296 ml) in CH$_2$Cl$_2$ (100 ml) at −78° C. The reaction was stirred at −78° C. for 15 minutes, followed by addition of Part G alcohol (10 g) in CH$_2$Cl$_2$ (100 ml) very slowly. Stirring was continued for 15 minutes at −78° C., then Et$_3$N (17.5 ml) was added dropwise at −78° C. and the reaction was gradually warmed to room temperature. Water (100 ml) was added and the water layer separated was further extracted with CH$_2$Cl$_2$ (240 ml×2). The combined CH$_2$Cl$_2$ layers were washed with H$_2$O (120 ml×3) and dried over MgSO$_4$. Filtration and evaporation of solvent gave a pale straw-colored oil, which was dried by azeotropic distillation with benzene several times. Title aldehyde in the form of a pale straw-colored foam (10.1 g) was obtained. This was used for the subsequent reaction without any purification.

J. (and J')
(Z)-7-[(cis)-2-[(S*)-2,2-Dimethyl-1,3-dioxolan-4-yl]-6-[(methylsulfonyl)oxy]-2-cyclohexen-1-yl]-5-heptenoic acid, methyl ester (J)

To (4-carboxybutyl)triphenylphosphonium bromide (15.948 g, 36 mmole) suspended in THF (150 ml) was added KO t-amylate in toluene (1.6M, 45 ml) dropwise at room temperature. After stirring for 6 hours at room temperature, a burgundy colored solution was obtained. Part H aldehyde (crude product, 10.1 g, 24 mmole) dissolved in THF (20 ml) was cooled to −30° C.~−40° C. The ylid solution (190 ml) was added dropwise over 40 minutes. The reaction was stirred at −40° C. for one hour and at room temperature overnight. The reaction was quenched with saturated NH$_4$Cl (40 ml) and brine (50 ml). The products were extracted with EtOAc (400 ml, 200 ml×3), which was dried over MgSO$_4$. Filtration and evaporation of solvents gave a straw-colored oil (15.3 g). This was suspended in Et$_2$O and treated with CH$_2$N$_2$ until the desired acid was esterified. The solvent was evaporated off in vacuo and the residue was purified by SiO$_2$ column (silica 60, 300 g) eluted with Et$_2$O/petroleum ether=1/1 and Et$_2$O to give title compound (4.8 g, 11.52 mmole, 48%). Depending upon the amount of the ylid used, compound (Z)-7-[(1α,2α,3α,6α)-2-[(S*)-2,2-dimethyl-1,3-dioxolan-4-yl]-3,6-bis[(methylsulfonyl)oxy]cyclohexyl]-5-heptenoic acid, methyl ester (J') can be obtained.

K.
(Z)-7-[(cis)-2-[(S*)-1,2-Dihydroxyethyl]-6-[(methylsulfonyl)oxy]cyclohexyl]-5-heptenoic acid, methyl ester To Part J compound (5.59 g, 13.45 mmole) dissolved in MeOH (56 ml) was added p-TsOH.H$_2$O (140 mg, 0.73 mmole), and the reaction was stirred at room temperature overnight. Saturated NaHCO$_3$ (10 ml) was added and MeOH was removed in vacuo. The residue was partitioned between EtOAc (100 ml) and brine (50 ml). The water layer was further extracted with EtOAc (100 ml×2). The combined EtOAc layers were washed with brine (50 ml) and dried over MgSO$_4$. Filtration and evaporation of solvent gave an oil (5.723 g), which was purified by SiO$_2$ column (silica 60, 150 g) eluted with 5% MeOH in CH$_2$Cl$_2$ to give the starting material (1.1 g, 2.6 mmole) and the desired title diol (3.3 g, 9.2 mmole, 85%).

L.
(Z)-7-[(cis)-2-Formyl-6-[(methylsulfonyl)oxy]-2-cyclohexen-1-yl]-5-heptenoic acid, methyl ester NaIO$_4$ (2.19 g, 10.1 mmole) suspended in H$_2$O (4 ml) was added to Part K diol (3.5 g, 9.2 mmole) in MeOH (36 ml) at 0° C. Stirring was continued for 1.5 hours at room temperature. 10% Na$_2$S$_2$O$_3$ (10 ml) was added to the reaction. The reaction was stirred for 10 minutes, and poured into Et$_2$O (100 ml) and H$_2$O (20 ml). The products were extracted into the Et$_2$O layer. The water layer was further extracted with Et$_2$O (50 ml×3). The combined Et$_2$O layers were washed with brine (50 ml) and dried over MgSO$_4$. Filtration and evaporation of solvents gave a pale yellow oil (3.1 g). The crude products were used for the subsequent reaction.

M.
(Z)-7-[(1α,2α,3α,6α)-3-(Acetylthio)-2-(dimethoxymethyl)-6-[(methylsulfonyl)oxy]cyclohexyl]-5-heptenoic acid, methyl ester CH$_3$COSH (9 ml, 0.102 mole) and Et$_3$N (9 ml, 0.065 mole) were added to the crude Part L product (3.1 g, 9 mmole) in CH$_2$Cl$_2$ (230 ml) at −20° C. The reaction was stirred for four hours at −20° C.~−10° C. and one hour at −10°~0° C. The reaction was poured into saturated NaHCO$_3$ and the products were extracted into CH$_2$Cl$_2$. The water layer was further extracted with CH$_2$Cl$_2$ (100 ml×3). The combined CH$_2$Cl$_2$ layers were washed with saturated NaHCO$_3$ and brine and dried over MgSO$_4$. Filtration and evaporation of solvent gave a crude oil (4.1 g). The crude oil (4.1 g) was dissolved in MeOH [300 ml, dried over Mg(OMe)$_2$] and treated with p-TsOH.H$_2$O (240 mg, 1.26 mmole) overnight at room temperature. NaHCO$_3$ (1.2 g) in H$_2$O (5 ml) was added to the reaction and MeOH was mostly removed in vacuo. The residue (~10 ml) was poured into Et$_2$O (150 ml) and H$_2$O (30 ml). The products were extracted into the Et$_2$O layer. The water layer was further extracted with Et$_2$O (100 ml×2). The combined Et$_2$O layers were washed with brine (50 ml) and dried over MgSO$_4$. Filtration and evaporation of solvent gave a pale yellow oil (4.2 g) which was purified by SiO$_2$ column (silica 60, 120 g) eluted with Et$_2$O/petroleum ether=1/1 and Et$_2$O/petroleum ether=2/1, to give desired title acetal (3.01 g, 6.4 mmole, 70% from Part H diol).

N.
(Z)-7-[(cis)-5-(Acetylthio)-6-(dimethoxymethyl)-1-cyclohexen-1-yl]-5-heptenoic acid, methyl ester To Part J mesylate (3.01 g, 6.43 mmole) dissolved in toluene (30 ml) was added 1,8-diazabicyclo[5.4.0]undec-7-ene (DBU) (5.5 g, 36 mmole). The reaction was warmed to 80° C. under magnetic stirring for 18 hours. The reaction was poured into Et$_2$O (130 ml) and washed with 0.5N-HCl (30 ml). The HCl wash was re-extracted with Et$_2$O (70 ml). The combined Et$_2$O layers were washed with 0.5N-HCl (30 ml), H$_2$O (30 ml×3) and dried over MgSO$_4$. Filtration and evaporation of the solvent gave a straw-colored oil (2.4 g), which was purified by SiO$_2$ column (silica 60, 80 g) eluted with Et$_2$O/petroleum ether=½ to give title thioacetate (1.41 g, 3.8 mmole, 58%) and disulfide described in Part O (0.58 g, 1.6 mmole, 25%) as colorless oils.

O.
5,5'-Bis[(Z)-7-[(cis)-6-(dimethoxymethyl)-1-cyclohexen-1-yl]-7-heptenoic acid, methyl ester]disulfide Solid NaOMe (84 mg, 1.6 mmole) was added to a magnetically stirred solution of Part N thioacetate (580 mg, 1.6 mmole) in MeOH (58 ml) at room temperature. Hydrolysis of thioacetate was completed in 2 hours at room temperature. O$_2$ was then bubbled through the reaction for 2 days. Saturated NH$_4$Cl (10 ml) and saturated CuSO$_4$ (100 μl) were added and O$_2$ was again bubbled through the reaction to complete disulfide formation. The reaction was concentrated in vacuo to remove most of MeOH. The products were extracted with Et$_2$O (100 ml, 50 ml). The combined Et$_2$O layers were washed with H$_2$O (30 ml×2) and dried over MgSO$_4$. Filtration and evaporation of the solvent gave a straw-colored oil (530 mg) which was purified by SiO$_2$ column (silica 60, 30 g) eluted with Et$_2$O/petroleum ether 1/4~1/2 to give the desired title disulfide (452 mg, 0.69 mmole, 85%) as a colorless oil.

Anal Calcd for C$_{34}$H$_{54}$O$_8$S$_2$: C, 62.35; H, 8.31; S, 9.79. Found: C, 62.28; H, 8.19; S, 9.77.

P.

[1β,2α(E),3α,4β]-7-[2-Chloro-3-dimethoxymethyl]-7-thiabicyclo[2.2.1]hept-2-yl]-5-heptenoic acid, methyl ester SO$_2$Cl$_2$ (63 μl, 0.784 mmole) in CH$_2$Cl$_2$ (5 ml) was added dropwise to a magnetically stirred solution of Part O disulfide (515 mg, 0.783 mmole) in CH$_2$Cl$_2$ (7.8 ml) at −78° C. over 30 minutes. Stirring was continued for 2 hours at −78° C. 10% Na$_2$S$_2$O$_3$ (10 ml) and saturated NaHCO$_3$ (10 ml) were added and the reaction was warmed to room temperature. The reaction was poured into CH$_2$Cl$_2$ (50 ml) and the products were extracted into the CH$_2$Cl$_2$ layer. The water layer was further extracted with CH$_2$Cl$_2$ (50 ml×2). The combined CH$_2$Cl$_2$ layers were washed with H$_2$O (30 ml×2) and dried over MgSO$_4$. Filtration and evaporation of solvent gave a colorless oil (568.5 mg, quantitative recovery).

Q.

[1β,2α(Z),3α,4β]-7-[3-(Dimethoxymethyl)-7-thiabicyclo[2.2.1]hept-2-yl]-5-heptenoic acid, methyl ester ZnCl$_2$ (313.2 mg, 2 mmole) and NaCNBH$_3$ (285 mg, 4 mmole) were dried under vacuum and heated (~50°-60° C.) for 20 minutes. Then Et$_2$O (20 ml) was added and the reaction was stirred for 30 minutes at room temperature, followed by an addition of Et$_3$N (320 μl, 2.3 mmole). After 30 minutes stirring at room temperature, Part P chloride (crude products, 568.5 mg) in Et$_2$O (10 ml) was added at room temperature. The reaction was stirred overnight at room temperature. Saturated NaHCO$_3$ (3 ml) was added and the reaction was poured into Et$_2$O (100 ml). The products were extracted into the Et$_2$O layer. The water layer was further extracted with Et$_2$O (100 ml). The combined Et$_2$O layers were washed with saturated NaHCO$_3$ (25 ml), H$_2$O (25 ml×2) and dried over MgSO$_4$. Filtration and evaporation of the solvent gave a colorless oil, which was purified by silica gel column (Baker silica gel for flash chromatography, 20 g) eluted with Et$_2$O/petroleum ether-1/4 to give the desired title product (379 mg, 1.155 mmole, 74% from part O disulfide.

Anal Calcd for C$_{17}$H$_{28}$O$_4$S: C, 62.16; H, 8.59; S, 9.76. Found: C, 62.13; H, 8.42; S, 9.67.

(R)

[1α,2β(5Z),3β,4α]-7-[3-Formyl-7-oxabicyclo[2.2.1]hept-2-yl]-5-heptenoic acid, methyl ester Acetal (prepared as described in Part Q) (850 mg, 2.59 mmol) was dissolved in acetone (20 ml) and 37% formaldehyde solution (53 ml). The solution was cooled in an ice bath and distilled CF$_3$COOH (7.4 ml) was added. After stirring at 0°-5° C. for 8 3/4 hours, saturated NaHCO$_3$ solution was added until no more gas evolution was observed. The product was extracted into ether (3×150 ml), washed with water (3×75 ml), dried (MgSO$_4$), filtered and freed of solvent in vacuo. The remaining colorless oil was twice dissolved in benzene and taken to dryness in vacuo leaving a colorless oil (821 mg) which was a mixture of the desired aldehyde ([1α,2β(5Z),3β,4α]-7-[3-formyl-7-thiabicyclo[2.2.1]hept-2-yl]-5-heptenoic acid, methyl ester) and the starting acetal.

S.

[1α,2β(5Z),3β,4α]-7-[3-Hydroxymethyl-7-thiabicyclo[2.2.1]hept-2-yl]-5-heptenoic acid, methyl ester The oil mixture from Part R was dissolved in methanol (30 ml) and cooled to 0° C. NaBH$_4$ (98 mg, 2.59 mmol) was added portionwise. After stirring at 0° C. for 20 minutes, most of the MeOH was removed in vacuo. The residue was partitioned between Et$_2$O (100 ml) and 1N HCl solution (30 ml). The aqueous layer was reextracted with Et$_2$O (2×30 ml). The combined Et$_2$O extracts were washed with saturated NaCl solution (2×30 ml), dried (MgSO$_4$) and freed of solvent in vacuo leaving an oil. This was chromatographed on silica gel (Baker silica gel-for flash chromatography, 40 g) eluting with ether-pet ether 1:1. After eluting the acetal from Part Q (172 mg, 20%), the desired title alcohol ester was obtained (497.4 mg, 67.6% from acetal from Part Q).

Anal Calcd for C$_{15}$H$_{24}$O$_3$S: C, 63.35; H, 8.51; S, 11.27. Found: C, 63.48; H, 8.56; S, 11.07.

TLC: silica gel, Et$_2$O-pet ether 1:1, UV+vanillin, R$_f$=0.22.

T.

[1β,2α(Z),3α,4β]-7-[3-[(Hexyloxy)methyl]-7-thiabicyclo[2.2.1]hept-2-yl]-5-heptenoic acid, hexyl ester A mixture of powdered KOH (450 mg, 8.05 mmol) in dry xylene (13 ml) was heated to reflux and 6.5 ml of solvent was distilled off. To the hot solution was added a mixture of Part S alcohol ester (241 mg, 0.848 mmol) and n-hexyl methanesulfonate (1.0 g, 5.55 mmol) in 12 ml of dry xylene. Xylene was again distilled off (7 ml) at which point a large amount of solid had precipitated. Xylene (10 ml) and n-hexyl methanesulfonate (~0.5 g) were added and the mixture was heated under reflux an additional 60 minutes. After cooling, the mixture was partitioned between saturated NH$_4$Cl solution (20 ml) and EtOAc (20 ml). The layers were separated and the aqueous layer was acidified to pH 2 with 1N HCl, then reextracted with EtOAc (2×20 ml). The combined EtOAc extracts were washed with saturated NaCl solution (20 ml), dried (MgSO$_4$), filtered and freed of solvent in vacuo. The residue was chromatographed on silica gel (Baker silica gel-for flash chromatography, 25 g), eluting with 10% ether in hexane to give the title hexyl ester (224 mg, 60%).

TLC: silica gel, Et$_2$O-hexane 1:4, UV+I$_2$, R$_f$=0.7.

EXAMPLE 2

[1β,2α(Z),3α,4β]-7-[3-[(Hexyloxy)methyl]-7-thiabicyclo[2.2.1]hept-2-yl]-5-heptenoic acid The Example 1 hexyl ester ([1β,2α(Z),3α,4β]-7-[3-[(hexyloxy)methyl]-7-thiabicyclo[2.2.1]hept-2-yl]-5-heptenoic acid, hexyl ester) (221 mg, 0.50 mmol) was dissolved in distilled THF (18 ml) in an argon atmosphere. 1N LiOH solution (2.5 ml) and H$_2$O (1 ml) were added and the mixture was stirred at room temperature. After 4 hours, a sample was checked by TLC and a large amount of the ester remained. Methanol (2 ml) was added at 5 hours, making the mixture more nearly homogeneous, and the mixture was left stirring overnight. 1N HCl solution (2.5 ml) and solid KCl were then added and the layers were separated. The aqueous layer was extracted with ether (3×100 ml). The combined organic layers (THF and ether) were washed with saturated NaCl solution (3×30 ml), dried (MgSO$_4$) and freed of solvent in vacuo leaving an oil. This was chromatographed on silica gel (Baker silica gel-for flash chromatography, 20 g) eluting with 2% MeOH in CH$_2$Cl$_2$ to give the title acid (154.7 mg, 87%).

Anal Calcd for C$_{20}$H$_{34}$O$_3$S: C, 67.75; H, 9.67; S, 9.04. Found: C, 67.92; H, 9.57; S, 8.89.

TLC: silica gel, 5% MeOH in CH$_2$Cl$_2$, UV+PMA, R$_f$=0.53.

EXAMPLE 3

[1β,2α(Z),3α,4β]-7-[3-[(Hexyloxy)methyl]-7-thiabicyclo[2.2.1]hept-2-yl]-5-heptenoic acid, 7-oxide Example 2 acid (69.2 mg, 0.195 mmol) was dissolved in methanol (8 ml) and the solution was cooled in an ice bath. A solution of NaIO$_4$ (46 mg, 0.21 mmol) in water (3 ml) was added. The mixture was left stirring overnight at room temperature. A 10% solution of Na$_2$S$_2$O$_3$ (1.5 ml) was added and the methanol was removed in vacuo. The residue was partitioned between saturated NaCl solution (10 ml) and CHCl$_3$ (50 ml). The aqueous layer was reextracted with CHCl$_3$ (2×30 ml). The combined organic layers were washed with saturated NaCl solution (10 ml), dried (MgSO$_4$) and freed of solvent in vacuo leaving an oil (72 mg). This was chromatographed on silica gel (Baker silica gel-for flash chromatography, 7 g) eluting with 2% MeOH in CH$_2$Cl$_2$ to give material (27.1 mg) which appeared by TLC to contain minor impurities. This was purified by HPLC (50 micron silica gel semi-prep column) eluting with 1.5 to 2.5% MeOH in CH$_2$Cl$_2$ to give title oxide compound (22.0 mg, 30%).

Anal Calcd for C$_{20}$H$_{34}$O$_4$S: C, 64.82; H, 9.24; S, 8.65. Found: C, 64.43; H, 9.17; S, 8.55.

TLC: Silica gel, 5% MeOH in CH$_2$Cl$_2$, PMA; R$_f$=0.15

EXAMPLE 4

[1β,2α(5Z),3α,4β]-7-[3-[(Hexylthio)methyl]-7-thiabicyclo[2.2.1]hept-2-yl]-5-heptenoic acid, methyl ester

A.

[1β,2α(5Z),3α,4β]-7-[3-[(Tosyloxy)methyl]-7-thiabicyclo[2.2.1]hept-2-yl]-5-heptenoic acid, methyl ester Alcohol ester from Example 1 Part S (namely, [1α,2β(5Z),3β,4α]-7-[3-hydroxymethyl-7-thiabicyclo[2.2.1]hept-2-yl]-5-heptenoic acid, methyl ester) (250.7 mg, 0.883 mmol) was dissolved in distilled pyridine (2.3 ml) and distilled CH$_2$Cl$_2$ (2.3 ml) in an argon atmosphere. After cooling in an ice bath, tosyl chloride (336 mg, 1.76 mmol) was added. The mixture was stirred cold for 30 minutes and overnight at room temperature. The reaction mixture was poured into ice water and stirred for 30 minutes. The product was extracted into ether (3×10 ml). The combined ether extracts were washed with 1N HCl (3×10 ml), saturated NaHCO$_3$ solution (5 ml) and saturated NaCl solution (5 ml), dried (MgSO$_4$), filtered and freed of solvent in vacuo leaving title tosylate as a colorless oil (370 mg, 95.5%) which was used without purification. TLC silica gel, ether-pet ether 1:1, UV+PMA, R$_f$=0.54.

B.

[1β,2α(5Z),3α,4β]-7-[3-[(Hexylthio)methyl]-7-thiabicyclo[2.2.1]hept-2-yl]-5-heptenoic acid, methyl ester Potassium tert.butoxide (61.0 mg, 0.54 mmol) was dissolved in distilled THF (4 ml) in an argon atmosphere. 1-Hexanethiol (0.23 ml, ~1.55 mmol) was added and a white precipitate formed immediately. A solution of Part A tosylate (187 mg, 0.426 mmol) in THF (5 ml) was added and the mixture was heated under reflux for 5 hours. After cooling, the mixture was partitioned between saturated NaHCO$_3$ solution (15 ml) and ether (15 ml). The aqueous layer was reextracted with ether (15 ml). The combined organic layers were washed with 0.5N NaOH (10 ml) and saturated NaCl solution (10 ml), dried (MgSO$_4$) and freed of solvent in vacuo leaving an oil. This was chromatographed on 20 g silica gel (Baker silica gel-for flash chromatography) eluting with 10% ether in petroleum ether to give the title methyl ester, 140.0 mg (85.4%). TLC silica gel, ether-petroleum ether 1:4, UV+PMA, R$_f$=0.7.

EXAMPLE 5

[1β,2α(5Z),3α,4β]-7-[3-[(Hexylthio)methyl]-7-thiabicyclo[2.2.1]hept-2-yl]-5-heptenoic acid The reaction was run under argon. Solvents were purged with argon prior to use. The Example 4 methyl ester (136 mg, 0.354 mmol) was dissolved in distilled THF (18 ml) and treated with 1N LiOH solution (3.5 ml) and water (3.5 ml). The mixture was stirred at room temperature 7.5 hours. 1N HCl solution (3.5 ml) and solid KCl were added. The layers were separated. The aqueous layer was reextracted with ether (3×25 ml). The combined organic layers (THF and Et$_2$O) were washed with saturated NaCl solution (3×20 ml), dried (MgSO$_4$), and freed of solvent in vacuo leaving an oil (131 mg). This was chromatographed on silica gel (15 g, Baker silica gel-for flash chromatography) eluting with 2% MeOH in CH$_2$Cl$_2$ to give the title acid, 86.5 mg (65.9%) and additional material (26.4 mg, 20.1%) which was slightly contaminated with a slower moving spot.

Anal Calcd for C$_{20}$H$_{34}$O$_2$S$_2$: C, 64.81; H, 9.25; S, 17.30. Found: C, 64.79; H, 9.21; S, 17.39.

TLC: silica gel, 4% MeOH in CH$_2$Cl$_2$, UV+I$_2$ R$_f$=0.54.

EXAMPLE 6

[1β,2α(5Z),3α,4β]-7-[3-[(Hexylthio)methyl]-7-thiabicyclo[2.2.1]hept-2-yl]-5-heptenoic acid, methyl ester, 7-oxide

A.

[1β,2α(5Z),3α,4β]-7-[3-[(Tosyloxy)methyl]-7-thiabicyclo[2.2.1]hept-2-yl]-5-heptenoic acid, methyl ester, 7-oxide

[1β,2α(5Z),3α,4β]-7-[3-[(Tosyloxy)methyl]-7-thiabicyclo[2.2.1]hept-2-yl]-5-heptenoic acid, methyl ester prepared as described in Example 4, Part A (176 mg, 0.40 mmol) was dissolved in methanol (15 ml) and the solution was cooled in an ice bath. A solution of NaIO$_4$ (109 mg, 0.51 mmol) in H$_2$O (6 ml) was added and the mixture was left stirring overnight at room temperature. A 10% solution of Na$_2$S$_2$O$_3$ (4 ml) was added and the methanol was removed in vacuo. The residue was extracted with CHCl$_3$ (3×50 ml) dried (MgSO$_4$), and freed of solvent in vacuo leaving title oxide as an oil (182 mg, quant.). After characterization (NMR, M.S.) this material was used without further purification. TLC: silica gel, 2% MeOH in CH$_2$Cl$_2$, PMA; R$_f$=0.14.

B.
[1β,2α(5Z),3α,4β]-7-[3-[(Hexylthio)methyl]-7-thiabicyclo[2.2.1]hept-2-yl]-5-heptenoic acid, methyl ester, 7-oxide Potassium t-butoxide (57.3 mg, 0.5 mmol) was dissolved in distilled THF (4 ml) in an argon atmosphere. 1-Hexanethiol (0.21 mg~1.45 mmol) was added and a white precipitate formed immediately. A solution of Part A oxide (0.40 mmol) in THF (6 ml) was added and the mixture was heated under reflux 4 hours. The cooled mixture was partitioned between EtOAc (15 ml) and saturated NaHCO$_3$ solution (15 ml). The aqueous layer was reextracted with EtOAc (15 ml). The combined organic layers were washed with 0.5N NaOH (10 ml) and saturated NaCl solution (10 ml), dried (MgSO$_4$) and freed of solvent in vacuo leaving an oil (185 mg). This material was first chromatographed on silica gel (Baker silica gel-for flash chromatography, 20 g) eluting with Et$_2$O and 1% MeOH in Et$_2$O to give 115 mg of material which was a mixture. This was then run on the HPLC 50 micron silica gel semi-prep column eluting with 0.5 to 2% MeOH in CH$_2$Cl$_2$ to give 89.8 mg of material which was a mixture. Chromatography on silica gel (Baker) eluting with EtOAc-hexane 1:1 gave 31.7 mg (20%) of clean title ester and an additional 36.5 mg of mixture (>50%, title ester).
TLC: silica gel, EtOAc, PMA R$_f$=0.58.

EXAMPLE 7

[1β,2α(5Z),3α,4β]-7-[3-[(Hexylthio)methyl]-7-thiabicyclo[2.2.1]hept-2-yl]-5-heptenoic acid, 7-oxide (Note: The reaction was run under argon; solvents were purged with argon prior to use). Example 6 methyl ester (31.7 mg, 0.079 mmol) was dissolved in distilled THF (4.5 ml) and treated with 1N LiOH solution (0.8 ml) and H$_2$O (0.8 ml). The mixture was stirred at room temperature 7.5 hours. 1N HCl solution (0.8 ml) was added followed by solid KCl. The layers were separated and the aqueous layer was reextracted with CHCl$_3$ (3×10 ml). The combined organic layers (THF and CHCl$_3$) were washed with saturated NaCl solution (5 ml), dried (MgSO$_4$) and freed of solvent in vacuo leaving an oil (28.5 mg). This was purified by chromatography on the HPLC 50 micron semi-prep silica gel column eluting with 15-30% THF in CH$_2$Cl$_2$ to give the title acid (26.3 mg, 86%) as an oil.
TLC: Silica gel, 4% MeOH in Et$_2$O, PMA; R$_f$=0.31.
Anal Calcd for C$_{20}$H$_{34}$O$_3$S$_2$: C, 62.13; H, 8.86; S, 16.59. Found: C, 61.99; H, 8.81; S, 16.41.

EXAMPLE 8

(1β,2α,3α,4β)-7-[3-[(Hexyloxy)methyl]-7-thiabicyclo[2.2.1]hept-2-yl]heptanoic acid Example 2 compound (183 mg, 0.54 mmol) dissolved in ethyl acetate (5 ml) is hydrogenated in the presence of 5% Pd/C (18 mg) under atmospheric pressure of hydrogen at room temperature. The reaction is filtered through a celite pad, which is washed with EtOAc (10 ml). The wash and the filtrate are combined, and concentrated in vacuo. The resulting oil is purified by HPLC (50 micron silica gel, semi-prep column) eluting with 15-30% THF in CH$_2$Cl$_2$ to give the title compound.

EXAMPLE 9

[1β,2α(5Z),3α,4β]-7-[3-[(Methyloxy)methyl]-7-thiabicyclo[2.2.1]hept-2-yl]-5-heptenoic acid Following the procedure of Examples 1 and 2 except substituting methyl methanesulfonate for n-hexyl methanesulfonate, the title compound is obtained.

EXAMPLE 10

(1β,2α,3α,4β)-7-[3-[(Butyloxy)methyl]-7-thiabicyclo[2.2.1]hept-2-yl]heptanoic acid Following the procedure of Examples 1, 2 and 8 except substituting n-butyl methanesulfonate for n-hexyl methanesulfonate, the title compound is obtained.

EXAMPLE 11

[1β,2α(5Z),3α,4β]-7-[3-[(Octyloxy)methyl]-7-thiabicyclo[2.2.1]hept-2-yl]-5-heptenoic acid Following the procedure of Examples 1 and 2 except substituting n-octyl methanesulfonate for n-hexyl methanesulfonate, the title compound is obtained.

EXAMPLE 12

[1β,2α(5Z),3α,4β]-7-[3-[(Phenyloxy)methyl]-7-thiabicyclo[2.2.1]hept-2-yl]-5-heptenoic acid (a) Phenol (1 mmol) is added to a solution of triphenylphosphine (1 mmol), diethylazodicarboxylate (1 mmol) and title G alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1β,2α(Z),3α,4β]-7-[3-[(phenyloxy)methyl]-7-thiabicyclo[2.2.1]hept-2-yl]-5-heptenoic acid, methyl ester.

(b) Following the procedure as set out in Example 2, the ester from part (a) is converted to the title compound.

EXAMPLE 13

[1β,2α(5Z),3α,4β]-7-[3-[(Ethyloxy)methyl]-7-thiabicyclo[2.2.1]hept-2-yl]-5-heptenoic acid Following the procedure of Examples 1 and 2 except substituting ethyl methanesulfonate for n-hexylmethane sulfonate, the title compound is obtained.

EXAMPLE 14

(1β,2α,3α,4β)-7-[3-[(Phenyloxy)methyl]-7-thiabicyclo[2.2.1]hept-2-yl)-5-heptanoic acid Following the procedure of Examples 12 and 8 except substituting the Example 12 compound for the Example 2 compound in Example 8, the title compound is obtained.

EXAMPLE 15

[1β,2α(5Z),3α,4β]-7-[3-[(Benzyloxy)methyl]-7-thiabicyclo[2.2.1]hept-2-yl]-5-heptenoic acid Following the procedure of Examples 1 and 2 except substituting benzyl methane sulfonate for n-hexylmethane sulfonate, the title compound is obtained.

EXAMPLE 16

(1β,2α,3α,4β)-7-[3-[(Benzyloxy)methyl]-7-thiabicyclo[2.2.1]hept-2-yl]heptanoic acid Following the procedure of Example 8 except substituting the Example 15 acid for the Example 2 acid, the title compound is obtained.

EXAMPLE 17

[1β,2α(5Z),3α,4β]-7-[3-[(Cyclohexyloxy)methyl]-7-thiabicyclo[2.2.1]hept-2-yl]-5-heptenoic acid Following the procedure of Examples 1 and 2 except substituting cyclohexyl methanesulfonate for n-hexyl methanesulfonate, the title compound is obtained.

EXAMPLE 18

[1β,2α(5Z),3α,4β]-7-[3-[(Cyclopentyloxy)methyl]-7-thiabicyclo[2.2.1]hept-2-yl]-5-heptenoic acid Following the procedure of Examples 1 and 2 except substituting cyclopentyl methanesulfonate for n-hexyl methanesulfonate, the title compound is obtained.

EXAMPLE 19

(1β,2α,3α,4β)-7-[3-[(Cyclohexyloxy)methyl]-7-thiabicyclo[2.2.1]hept-2-yl]heptanoic acid Following the procedure of Example 8 except substituting the Examples 17 acid for the Example 2 acid, the title compound is obtained.

EXAMPLE 20

[1β,2α(5Z),3α,4β]-7-[3-[2-(Hexyloxy)ethyl]-7-thiabicyclo[2.2.1]hept-2-yl]-5-heptenoic acid

A.

[1β,2α(5Z),3α,4β]-7-[3-[(2-Oxo)ethyl]-7-thiabicyclo[2.2.1]hept-2-yl]-5-heptenoic acid, methyl ester Into a dry 100 ml round bottom 3-necked flask containing a stir bar is added dried 12.9 g (37.7 mmoles) methoxymethyltriphenylphosphonium chloride ((C$_6$H$_5$)$_3$P$^+$-CH$_2$OCH$_3$Cl$^-$) and 235 ml distilled toluene (stored over molecular sieves). The resulting suspension is stirred in an ice-bath, under argon, until cold and then a 1.55M solution of 18.3 ml (28.3 mmol) of potassium t-amylate in toluene was added dropwise. A bright red solution formed which is stirred at 0° C. for an additional 35 minutes. Thereafter, a solution of 5.26 g (18.8 mmol) [1β,2α(5Z),3α,4β]-7-(3-formyl)-7-thiabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture is immediately poured into 200 ml saturated NH$_4$Cl, and extracted with ether (4×200 ml). The combined ether phases are washed with NaCl saturated solution, and dried (MgSO$_4$) and concentrated to yield a yellow oil in a white crystalline solid (phosphine oxide). The white solid is triturated with EtOAc and the mother liquor is purified by chromatography on an LPS-1 silica column. The fractions obtained are (A) [β,2α(5Z), 3α,4β]-7-[[3-(2-oxo)ethyl]bicyclo[2.2.1]hept-2-yl]-5-heptenoic acid, methyl ester, (B) [1β,2α(5Z),3α,4β]-7-[3-(2-methoxy)ethenyl]bicyclo[2.2.1]hept-2-yl]-5-heptenoic acid, methyl ester, and (C) [1β,2α(Z),3α,4β]-7-[[3-(2,2-dimethoxy)-ethyl]bicyclo[2.2.1]hept-2-yl]-5-heptenoic acid, methyl ester.

Compounds (B) and (C) are each treated with trifluoroacetic acid to convert each to compound (A).

B.

[β2α(5Z),3α,4β]-7-[3-(2-Hydroxyethyl)-7-thiabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1β,2α(5Z),3α,4β]-7-[3-[2-(Hexyloxy)ethyl]-7-thiabicyclo[2.2.1]hept-2-yl]-5-heptenoic acid Following the procedure of Examples 1 and 2 except substituting the above part B alcohol for the alcohol used in Example 1, Part S, the title compound is obtained.

EXAMPLE 21

(1β,2α,3α,4β)-7-[3-[2-(Hexyloxy)ethyl]-7-thiabicyclo[2.2.1]hept-2-yl]heptanoic acid Following the procedure of Examples 20 and 8 except substituting (1β, 2α,3α,4β)-7-[(3-formyl)-7-thiabicyclo[2.2.1]hept-2-yl]-5-heptanoic acid, methyl ester for [1β,2α(5Z),3α,4β]-7-[(3-formyl)-7-thiabicyclo[2.2.1]hept-2-yl]-5-heptenoic acid, methyl ester, the title compound is obtained.

EXAMPLE 22

(1β,2α,3α,4β)-7-[3-[2-(Phenyloxy)ethyl]bicyclo[2.2.1]hept-2-yl]heptanoic acid

Following the procedure of Examples 12, 21 and 8 except substituting (1β,2α,3α,4β)-7-[3-(2-hydroxyethyl)-7-thiabicyclo[2.2.1]hept-2-yl]heptanoic acid, methyl ester for [1β,2α(5Z),3α,4β]-7-[3-(hydroxymethyl)-7-thiabicyclo[2.2.1]hept-2-yl]-5-heptenoic acid, methyl ester, the title compound is obtained.

EXAMPLE 23

[1β,2α(5Z),3α,4β]-7-[3-[2-(Benzyloxy)ethyl]-7-thiabicyclo[2.2.1]hept-2-yl]-5-heptenoic acid Following the procedure of Example 20 except substituting benzyl methanesulfonate for n-hexyl methanesulfonate, the title compound is obtained.

EXAMPLE 24

[1β,2α(5Z), 3α,4β]-7-[3-[2-(Cyclopentyloxy)ethyl]-7-thiabicyclo[2.2.1]hept-2-yl]-5-heptenoic acid Following the procedure of Example 20 except substituting cyclopentyl methanesulfonate for n-hexyl methanesulfonate, the title compound is obtained.

EXAMPLE 25

[1β,2α(5Z),3α,4β]-7-[3-[2-(Cyclohexyloxy)ethyl]-7-thiabicyclo[2.2.1]hept-2-yl]-5-heptenoic acid Following the procedure of Example 20 except substituting cyclohexyl methanesulfonate for n-hexyl methanesulfonate, the title compound is obtained.

EXAMPLE 26

[1β,2α(5Z),3α,4β]-7-[3-[4-(Hexyloxy)butyl]-7-thiabicyclo[2.2.1]hept-2-yl]-5-heptenoic acid

A.
[1β,2α(5Z),3α,4β]-7-[[3-(3-Oxo)propyl]bicyclo[2.2.1-]hept-2-yl]-5-heptenoic acid, methyl ester Following the procedure of Example 20, part A except substituting [1β,2α(5Z),3α,4β]-7-[[3-(2-oxo)ethyl]-7-thiabicyclo[2.2.1]hept-2-yl]-5-heptenoic acid, methyl ester for [1β,2α(5Z), 3α,4β]-7-[3-formyl-7-thiabicyclo[2.2.1]hept-2-yl]-5-heptenoic acid, methyl ester, the title A compound is obtained.

B.
[1β,2α(5Z),3α,4β]-7-[3-(4-Oxo)butyl-7-thiabicyclo[2.2.1]hept-2-yl]-5-heptenoic acid, methyl ester Following the procedure of Example 20, part A, except substituting the aldehyde from part A above for [1β,2α(5Z),3α,4β]-7-[3-formyl-7-thiabicyclo[2.2.1-]hept-2-yl]-5-heptenoic acid, methyl ester, the title B compound is obtained.

C.
[β,2α(5Z),3α,4β]-7-[3-(4-Hydroxybutyl)-7-thiabicyclo[2.2.1]hept-2-yl]-5-heptenoic acid, methyl ester Following the procedure of Example 20, part B, except substituting the title B aldehyde for [1β,2α(5Z)-,3α,4β]-7-[[3-(2-oxo)ethyl]7-thiabicyclo[2.2.1]hept-2-yl]-5-heptenoic acid, methyl ester, the title C alcohol is obtained.

D.
[1β,2α(5Z),3α,4β]-7-[3-[4-(Hexyloxy)butyl]-7-thiabicyclo[2.2.1]hept-2-yl]-5-heptenoic acid Following the procedure of Examples 1 and 2, except substituting the above part C alcohol for the alcohol used in Example 1, Part S, the title compound is obtained.

EXAMPLE 27

[1β,2α(5Z),3α,4β]-7-[3-[4-(Cyclohexyloxy)butyl]-7-thiabicyclo[2.2.1]hept-2-yl]-5-heptenoic acid Following the procedure of Example 26 except substituting cyclohexyl methanesulfonate for n-hexyl methanesulfonate, the title compound is obtained.

EXAMPLE 28

[1β,2α(5Z),3α,4β]-7-[3-[4-(Phenyloxy)butyl]-7-thiabicyclo[2.2.1]hept-2-yl]-5-heptenoic acid Following the procedure of Examples 12 and 26 except substituting [1β,2α(5Z),3α,4β]-7-[3-(4-hydroxybutyl)-7-thiabicyclo[2.2.1]hept-2-yl]-5-heptenoic acid, methyl ester for [1β,2α(5Z),3α,4β]-7-[3-(hydroxymethyl)-7-thiabicyclo[2.2.1]hept-2-yl]-5-heptenoic acid, methyl ester, the title compound is obtained.

EXAMPLE 29

[1β,2α(5Z),3α,4β]-7-[3-[4-(Benzyloxy)butyl]-7-thiabicyclo[2.2.1]hept-2-yl]-5-heptenoic acid Following the procedure of Example 26 except substituting benzyl methanesulfonate for n-hexyl methanesulfonate, the title compound is obtained.

EXAMPLE 30

Tris(hydroxymethyl)aminomethane salt of [1β,2α(5Z),3α,4β]-7-[3-[(Hexyloxy)methyl]-7-thiabicyclo[2.2.1]hept-2-yl]-5-heptenoic acid A solution of the compound formed in Example 2 in methanol is treated with an equivalent amount of tri(hydroxymethyl)aminomethane. The solvent is removed by evaporation to yield the title compound.

EXAMPLE 31

[1β,2α(5Z),3α,4β]-7-[3-[(Methylthio)methyl]-7-thiabicyclo[2.2.1]-hept-2-yl]-5-heptenoic acid Following the procedure of Examples 4 and 5 except substituting methanethiol for 1-hexanethiol, the title compound is obtained.

EXAMPLE 32

[1β,2α(5Z),3α,4β]-7-[3-[(Propylthio)methyl]-7-thiabicyclo[2.2.1]hept-2-yl]-5-heptenoic acid Following the procedure of Examples 4 and 5 except substituting 1-propanethiol for 1-hexanethiol, the title compound is obtained.

EXAMPLE 33

(1β,2α,3α,4β)-7-[3-[(Butylthio)methyl]-7-thiabicyclo[2.2.1]hept-2-yl]heptanoic acid Following the procedure of Examples 4, 5 and 8 except substituting 1-butanethiol for 1-hexanethiol, the title compound is obtained.

EXAMPLE 34

[1β,2α(5Z),3α,4β]-7-[3-[(OCtylthio)methyl]-7-thiabicyclo[2.2.1]hept-2-yl]-5-heptenoic acid Following the procedure of Examples 4 and 5 except substituting 1-octanethiol for 1-hexanethiol, the title compound is obtained.

EXAMPLE 35

[1β,2α(5Z),3α,4β]-7-[3-[(Phenylthio)methyl]-7-thiabicyclo[2.2.1]hept-2-yl]-5-heptenoic acid Following the procedure of Examples 4 and 5 except substituting thiophenol for 1-hexanethiol, the title compound is obtained.

EXAMPLE 36

(1β,2α,3α,4β)-7-[3-[(Phenylthio)methyl]-7-thiabicyclo[2.2.1]hept-2-yl]heptanoic acid Following the procedure of Examples 4, 5 and 8 except substituting thiophenol for 1-hexanethiol, the title compound is obtained.

EXAMPLE 37

[1β,2α(5Z),3α,4β]-7-[3-[(Ethylthio)methyl]-7-thiabicyclo[2.2.1]hept-2-yl]-5-heptenoic acid Following the procedure of Examples 4 and 5 except substituting ethanethiol for 1-hexanethiol, the title compound is obtained.

EXAMPLE 38

[1β,2α(Z),3α,4β]-7-[3-[(Benzylthio)methyl]-7-thiabicyclo[2.2.1]hept-2-yl]-5-heptenoic acid Following the procedure of Examples 4 and 5 except substituting benzylthiol for 1-hexanethiol, the title product is obtained.

EXAMPLE 30

[1β,2α(5Z),3α,4β]-7-[3-[(Cyclohexylthio)methyl]-7-thiabicyclo[2.2.1]hept-2-yl]-5-heptenoic acid Following the procedure of Examples 4 and 5 except substituting cuclohexanethiol for 1-hexanethiol, the title compound is obtained.

EXAMPLE 40

(1β,2α,3α,4β)-7-[3-[(Cyclohexylthio)methyl]-7-thiabicyclo[2.2.1]hept-2-yl]heptanoic acid Following the procedure of Examples 4, 5 and 8 except substituting cyclohexanethiol for 1-hexanethiol, the title product is obtained.

EXAMPLE 41

[1β,2α(5Z),3α,4β]-7-[3-[2-(Hexylthio)ethyl]-7-thiabicyclo[2.2.1]hept-2-yl]-5-heptenoic acid Following the procedure of Examples 20 , 4 and 5 except substituting the Example 20 part B alcohol for the alcohol used in Example 3, the title compound is obtained.

EXAMPLE 42

(1β,2α,3α,4β)-7-[3-[2-(Hexylthio)ethyl]-7-thiabicyclo[2.2.1]hept-2-yl]heptanoic acid Following the procedure of Examples 20, 21 and 4 and 5 except substituting the Example 20 Part B alcohol for the alcohol used in Example 4 Part A, the title compound is obtained.

EXAMPLE 43

[1β,2α(5Z),3α,4β]-7-[3-[2-(Phenylthio)ethyl]-7-thiabicyclo[2.2.1]hept-2-yl]-5-heptenoic acid Following the procedure of Examples 20 and 21 except substituting the Example 20 Part B alcohol for the alcohol used in Example 4, Part A and substituting thiophenol for 1-hexanethiol (of Example 4), the title compound is obtained.

EXAMPLE 44

(1β,2α,3α,4β)-7-[3-[2-(Phenylthio)ethyl]-7-thiabicyclo[2.2.1]hept-2-yl]heptanoic acid Following the procedure of Examples 20, 21 and 4 and 5 except substituting the Example 20 Part B alcohol for the alcohol used in Example 4, Part A and substituting thiophenol for 1-hexanethiol (of Example 4), the title compound is obtained.

EXAMPLE 45

[1β,2α(5Z),3α,4β]-7-[3-[2-(Benzylthio)ethyl]-7-thiabicyclo[2.2.1]hept-2-yl]-5-heptenoic acid Following the procedure of Examples 20, 4 and 5 except substituting the Example 20 Part B alcohol for the alcohol used in Example 4, Part A and substituting benzylthiol for 1-hexanethiol (of Example 4), the title compound is obtained.

EXAMPLE 46

[1β,2α(5Z),3α,4β]-7-[3-[2-(Cyclopentylthio)ethyl]-7-thiabicyclo[2.2.1]hept-2-yl]-5-heptenoic acid Following the procedure of Examples 20, 4 and 5 except substituting the Example 20B alcohol for the alcohol used in Example 4, Part A and substituting cyclopentanethiol for 1-hexanethiol (of Example 4), the title compound is obtained.

EXAMPLE 47

[1β,2α(5Z),3α,4β]-7-[3-[2-(Cyclohexylthio)ethyl]-7-thiabicyclo[2.2.1]hept-2-yl]-5-heptenoic acid Following the procedure of Example 21 except substituting the Example 20B alcohol for the alcohol used in Example 4, Part A and substituting cyclohexanethiol for 1-hexanethiol (of Example 4), the title product is obtained.

EXAMPLE 48

[1β,2α(5Z),3α,4β]-7-[3-[4-(Hexylthio)butyl]-7-thiabicyclo[2.2.1]hept-2-yl]-5-heptenoic acid Following the procedure of Examples 26, 4 and 5 except substituting the Example 26 part C alcohol for the alcohol used in Example 4, the title compound is obtained.

EXAMPLE 49

[1β,2α(5Z),3α,4β]-7-[3-[4-(Cyclohexylthio)butyl]-7-thiabicyclo[2.2.1hept-2-yl]-5-heptenoic acid Following the procedure of Example 48 except substituting cyclohexanethiol for 1-hexanethiol, the title compound is obtained.

EXAMPLE 50

[1β,2α(5Z),3α,4β]-7-[3-[4-(Phenylthio)butyl]-7-thiabicyclo[2.2.1]hept-2-yl]-5-heptenoic acid Following the procedure of Example 48 except substituting thiophenol for 1-hexanethiol, the title compound is obtained.

EXAMPLE 51

[1β,2α(5Z),3α,4β]-7-[3-[4-(Benzylthio)butyl]-7-thiabicyclo[2.2.1]hept-2-yl]-5-heptenoic acid Following the procedure of Example 48 except substituting benzylthiol for 1-hexanethiol, the title compound is obtained.

EXAMPLE 52

[1β,2α(5Z),3α,4β]-7-[3-[(Hexylsulfinyl)methyl]-7-thiabicyclo[2.2.1]hept-2-yl]-5-heptenoic acid, 7-oxide.

NaIO$_4$ (194.7 mg, 0.91 mmol) dissolved in H$_2$O (10 ml) is added to [β,2α(5Z),3α,4β]-7-[3-[(hexylthio)methyl]-7-thiabicyclo[2.2.1]hept-2-yl]-5-heptenoic acid (prepared as described in Example 5) 135.1 mg, 0.364 mmol (dissolved in MeOH (20 ml). The reaction is stirred overnight at room temperature. A 10% Na$_2$S$_2$O$_3$ solution (3 ml) is added and MeOH is removed in vacuo. The residue is partitioned between saturated NaCl solution (10 ml) and CHCl$_3$ (50 ml). The water layer is reextracted with CHCl$_3$ (30 ml×2).The combined CHCl$_3$ layers are washed with saturated NaCl solution (10 ml) and dried over MgSO$_4$. Filtration and evaporation of solvent give a crude product which is purified by silica gel chromatography to afford the title compound.

EXAMPLE 53

[1β,2α(5Z),3α,4β]-7-[3-[(Hexylsulfonyl)methyl]-7-thiabicyclo[2.2.1]hept-2-yl]-5-heptenoic acid, 7-oxide 90% $H_2O_2$ (76 mg, 2 mmol) is added to a magnetically stirred solution of [1β,2α(5Z),3α,4β]-7-[3-[(hexylthio)methyl]-7-thiabicyclo[2.2.1]hept-2-yl]-5-heptenoic acid (prepared as described in Example 5) (135.0 mg, 0.364 mmol) dissolved in MeOH (20 ml). The reaction is stirred overnight at room temperature. A 10% $Na_2S_2O_3$ solution (5 ml) is added and MeOH is removed in vacuo. The residue is partitioned between saturated NaCl solution (10 ml) and $CHCl_3$ (50 ml). The water layer is re-extracted with $CHCl_3$ (30 ml×2). The combined $CHCl_3$ layers are washed with saturated NaCl solution (10 ml) and dried over $MgSO_4$. Filtration and evaporation of solvent give a crude product. Purification of the crude product by silica gel chromatograph yields the title compound.

EXAMPLE 54

[1β,2α(5Z),3α,4β]-7-[3-[(Ethylsulfinyl)methyl]-7-thiabicyclo[2.2.1]hept-2-yl]-5-heptenoic acid, 7-oxide Following the procedure of Examples 4, 5, and 52 except substituting ethylmercaptan for 1-hexanethiol, the title compound is obtained.

EXAMPLE 55

(1β,2α,3α,4β)-7-[3-[(Heptylsulfinyl)methyl]-7-thiabicyclo[2.2.1]hept-2-yl]heptanoic acid, 7-oxide Following the procedure of Examples 4, 5, 8 and 52 except substituting 1-heptanethiol for 1-hexanethiol, the title compound is obtained.

EXAMPLE 56

[β,2α(5Z),3α,4β]-7-[3-[(Benzylsulfinyl)methyl]-7-thiabicyclo[2.2.1]hept-2-yl]-5-heptenoic acid, 7-oxide Following the procedure of Examples 4, 5 and 52 except substituting benzylmercaptan for 1-hexanethio, the title compound is obtained.

EXAMPLE 57

[1β,2α(5Z),3α,4β]-7-[3-[[(Cyclohexylmethyl)sulfinyl]methyl]-7-thiabicyclo[2.2.1]hept-2-yl]-5-heptenoic acid, 7-oxide Following the procedure of Examples 4, 5 and 52 except substituting cyclohexylmethyl mercaptan for 1-hexanethiol, the title compound is obtained.

EXAMPLE 58

[1β,2α(5Z),3α,4β]-7-[3-[[(Cyclopentylethyl)sulfinyl]methyl]-7-thiabicyclo[2.2.1]hept-2-yl]-5-heptenoic acid, 7-oxide.

Following the procedures of Examples 4, 5 and 52 except substituting cyclopentylethyl mercaptan for 1-hexanethiol, the title compound is obtained.

EXAMPLE 59

[1β,2α(5Z),3α,4β]-7-[3-[(Octylthio)methyl]-7-thiabicyclo[2.2.1]hept-2-yl]-5-heptenoic acid, 7-oxide Following the procedure of Examples 4, 5, 6, and 7 except substituting octylmercaptan for 1-hexanethiol, the title compound is obtained.

EXAMPLE 60

[1β,2α(5Z),3α,4β]-7-[3-[(Propylthio)methyl]-7-thiabicyclo[2.2.1]-hept-2-yl]-5-heptenoic acid, 7-oxide Following the procedure of Examples 4, 5, 6, 7 and 53 except substituting propylmercaptan for 1-hexanethiol, the title compound is obtained.

EXAMPLE 61

[1β,2α(5Z),3α,4β]-7-[3-[(Phenylthio)methyl]-7-thiabicyclo[2.2.1]hept-2-yl]-5-heptenoic acid, 7-oxide Following the procedure of Examples 4, 5, 6, and 7 except substituting phenylmercaptan for 1-hexanethiol, the title compound is obtained.

EXAMPLE 62

[1β,2α(5Z),3α,4β]-7-[3-[(Benzylthio)methyl]-7-thiabicyclo[2.2.1]hept-2-yl]-5-heptenoic acid, 7-oxide Following the procedure of Examples 4, 5, 6 and 7 except substituting benzylmercaptan for 1-hexanethiol, the title compound is obtained.

EXAMPLE 63

[1β,2α(5Z),3α,4β]-7-[3-[(Cyclohexylthio)methyl]-7-thiabicyclo[2.2.1]hept-2-yl]-5-heptenoic acid, 7-oxide Following the procedure of Examples 4, 5, 6 and 7 except substituting cyclohexylmercaptan for 1-hexanethiol, the title compound is obtained.

EXAMPLE 64

(1β,2α,3α,4β)-7-[3-[[(Cyclopropylmethyl)sulfinyl]methyl]-7-thiabicyclo[2.2.1]hept-2-yl]heptanoic acid, 7-oxide Following the procedure for Examples 4, 5, 8, and 53 except substituting cyclopropylmercaptan for 1-hexanethiol, the title compound is obtained.

EXAMPLE 65

[1β,2α(5Z),3α,4β]-7-[3-[2-(Pentylsulfinyl)ethyl]-7-thiabicyclo[2.2.1]hept-2-yl]-5-heptenoic acid, 7-oxide Following the procedure of Examples 41, 4, 5, and 52 except substituting 1-pentanethiol for 1-hexanethiol, the title compound is obtained.

EXAMPLE 66

[1β,2α(5Z),3α,4β]-7-[3-[2-(Phenylthio)ethyl]-7-thiabicyclo[2.2.1]hept-2-yl]-5-heptenoic acid, 7-oxide Following the procedure of Examples 41, 4, 5, 6 and 7 except substituting phenylmercaptan for 1-hexanethiol, the title compound is obtained.

EXAMPLE 67

[1β,2α(5Z),3α,4β]-7-[3-[2-(Cyclohexylthio)ethyl]-7-thiabicyclo[2.2.1]hept-2-yl]-5-heptenoic acid, 7-oxide Following the procedure of Examples 41, 4, 5 and 55 except substituting cyclohexylmercaptan for 1-hexanethiol, the title compound is obtained.

EXAMPLE 68

[1β,2α(5Z),3α,4β]-7-[3-[2-(Benzylthio)ethyl]-7-thiabicyclo[2.2.1]hept-2-yl]-5-heptenoic acid, 7-oxide Following the procedure for 41, 4, 5, 6 and 7 except substituting benzylmercaptan for 1-hexanethiol, the title compound is obtained.

EXAMPLE 69

[1β,2α(5Z),3α,4β]-7-[3-[(Methyloxy)methyl]-7-thiabicyclo[2.2.1]hept-2-yl]-5-heptenoic acid, 7-oxide NaIO$_4$ (29 mg, 0.135 mmol) in H$_2$O (2.9 ml) is added to a magnetically stirred solution of [1α,2β(5Z),3β,4α]-7-[3-[(methyloxy)methyl]-7-thiabicyclo[2.2.1]hept-2-yl]-5-heptenoic acid (prepared as described in Example 9, 370 mg, 0.123 mmole) in MeOH (6 ml) at 0° C. Stirring is continued for 0° C. for 8 hours and at room temperature overnight. 10% Na$_2$S$_2$O$_3$ (1 ml) is added and the reaction is concentrated to remove MeOH in vacuo. The residue is partitioned between brine (5 ml) and EtOAc (30 ml×3). The combined EtOAc layers are washed with brine (10 ml). The combined water layers are then extracted with CHCl$_3$ (15 ml×3). The EtOAc layer and the combined CHCl$_3$ layers are dried separately over MgSO$_4$. After filtration of MgSO$_4$, the EtOAc layer and the CHCl$_3$ layer are combined and concentrated in vacuo to give product. This is purified by HPLC (50μ silica gel, semi-prep. column) eluted with 2–6% MeOH in CH$_2$Cl$_2$ linear gradient to give title 7-oxide.

EXAMPLE 70

(1β,2α,3α,4β)-7-[3-[(Butyloxy)methyl]-7-thiabicyclo[2.2.1]hept-2-yl]heptanoic acid, S-oxide Following the procedure of Examples 1, 2, 8 and 69 except substituting n-butyl methanesulfonate for n-hexyl methanesulfonate, the title compound is obtained.

EXAMPLE 71

[1β,2α(5Z),3α,4β]-7-[3-[(Octyloxy)methyl]-7-thiabicyclo[2.2.1]hept-2-yl]-5-heptenoic acid, S-oxide Following the procedure of Examples 1, 2 and 69 except substituting n-octyl methanesulfonate for n-hexyl methanesulfonate, the title compound is obtained.

EXAMPLE 72

[1β,2α(5Z),3α,4β]-7-[3-[(Ethyloxy)methyl]-7-thiabicyclo[2.2.1]hept-2-yl]-5-heptenoic acid, S-oxide Following the procedure of Examples 1, 2 and 69 except substituting ethyl methanesulfonate for n-hexyl methanesulfonate, the title compound is obtained.

EXAMPLE 73

(1β,2α,3α,4β)-7-[3-[(Phenyloxy)methyl]-7-thiabicyclo[2.2.1]hept-2-yl]-5-heptanoic acid, S-oxide Following the procedure of Examples 12, 8 and 69 except substituting the Example 12 compound for the Example 2 compound in Example 8, the title compound is obtained.

EXAMPLE 74

[1β,2α(5Z),3α,4↑]-7-[3-[(Benzyloxy)methyl]-7-thiabicyclo[2.2.1]hept-2-yl]-5-heptenoic acid, S-oxide Following the procedure of Examples 1, 2 and 69 except substituting benzyl methanesulfonate for n-hexyl methanesulfonate, the title compound is obtained.

EXAMPLE 75

[1β,2α(5Z),3α(E),4β]-7-[3-[[(4-Phenyl-2-butenyl)thio]methyl]-7-thiabicyclo[2.2.1]hept-2-yl]-5-heptenoic acid Following the procedure of Examples 4 and 5 except substituting (2E)-4-phenylbut-2-ene-1-thiol for 1-hexanethiol, the title compound is obtained.

EXAMPLE 76

[1β,2α(5Z),3⊕(E),4β]-7-[3-[[(3-Cyclohexyl-2-propenyl)oxy]methyl]-7-thiabicyclo[2.2.1]hept-2-yl]-5-heptenoic acid Following the procedure of Example 1 except substituting (2E)-3-cyclohexyl-prop-2-enylmesylate for n-hexyl methanesulfonate, the title compound is obtained.

EXAMPLE 77

(1β,2α,3α,4β)-7-[3-[[(4-Cyclohexyl-2-butenyl)thio]methyl]-7-thiabicyclo[2.2.1]hept-2-yl]heptanoic acid Following the procedure of Examples 4, 5 and 8 except substituting 4-cyclohexyl-but-2-ene-1-thiol for 1-hexanethiol, the title compound is obtained.

EXAMPLE 78

[1β,2α(5Z),3α,4β]-7-[3-[[(2,3-Dimethyl-2-heptenyl)oxy]methyl]-7-thiabicyclo[2.2.1]hept-2-yl]-5-heptenoic acid Following the procedure of Example 32 except substituting 2,3-dimethyl-hept-2-enyl methanesulfonate for n-hexyl methanesulfonate, the title compound is obtained.

Example 79

]1β,2α(5Z),3α,4β]-7-[3-[[(3-Ethyl-3-octenyl)thio]methyl]-7-thiabicyclo[2.2.1]hept-2-yl]-5-heptenoic acid Following the procedure of Examples 4 and 5 except substituting 3-ethyl-oct-3-ene-1-thiol for 1-hexanethiol, the title compound is obtained.

EXAMPLE 80

(1β,2α,3α,4β)-7-[3-[(5-Phenyl-4-pentenyl)oxy]methyl]-7-thiabicyclo[2.2.1]hept-2-yl]heptanoic acid Following the procedure of Examples 1, 2 and 8 except substituting 5-phenyl-pent-4-enyl mesylate for n-hexyl methanesulfonate, the title compound is obtained.

EXAMPLE 81

[1β,2α(5Z),3α,4β]-7-[3-[[(8-Phenyl-5-octynyl)thio]methyl]-7-thiabicyclo[2.2.1]hept-2-yl]-5-heptenoic acid Following the procedure of Examples 4 and 5 except substituting 8-phenyl-oct-5-yne-1-thiol for 1-hexanethiol, the title compound is obtained.

EXAMPLE 82

[1β,2α(5Z),3α,4β]-7-[3-[[(9-Cyclohexyl-3-nonynyl)oxy]methyl]-7-thiabicyclo[2.2.1]hept-2-yl]-5-heptenoic acid Following the procedure of Example 1 except substituting 9-cyclohexyl-non-3-ynyl methanesulfonate for n-hexyl methanesulfonate, the title compound is obtained.

EXAMPLE 83

(1β,2α,3α,4β)-7-[3-[[(6-Heptynyl)thio]methyl]-7-thiabicyclo[2.2.1]hept-2-yl]heptanoic acid Following the procedure of Examples 4, 5 and 8 except substituting hept-6-yne-1-thiol for 1-hexanethiol, the title compound is obtained.

EXAMPLE 84

[1β,2α(5Z),3α,4β]-7-[3-[[2-(3-Phenyl-2-propenyl)thio]ethyl]-7-thiabicyclo[2.2.1]hept-2-yl]-5-heptenoic acid Following the procedure of Examples 20, 4 and 5 except substituting the Example 20 part B alcohol for the alcohol used in Example 4 Part B and substituting 3-phenyl-prop-2-ene-1-thiol for 1-hexanethiol, the title compound is obtained.

EXAMPLE 85

(1β,2α,3α,4β)-7-[3-[[2-(3-Phenyl-2-propenyl)thio]ethyl]-7-thiabicyclo[2.2.1]hept-2-yl]heptanoic acid Following the procedure of Example 8 except substituting the Example 84 compound for the Example 1 compound, the title compound is obtained.

EXAMPLE 86

[1β,2α(5Z),3α,4β]-7-[3-[[2-(6-Phenyl-3-hexynyl)oxy]ethyl]-7-thiabicyclo[2.2.1]hept-2-yl]-5-heptenoic acid Following the procedure of Examples 20, 1 and 2 except substituting 6-phenyl-hex-3-ynyl methanesulfonate for n-hexyl methanesulfonate, the title compound is obtained.

EXAMPLE 87

(1β,2α,3α,4β)-7-[3-[[2-(2-Ethyl-3-methyl-2-heptenyl)thio]ethyl]-7-thiabicyclo[2.2.1]hept-2-yl]heptanoic acid Following the procedure of Examples 4, 5, 8 and 20 except substituting 2-ethyl-3-methylhept-2-ene-1-thiol for 1-hexanethiol, the title compound is obtained.

EXAMPLE 88

[1β,2α(5Z),3α,4β]-7-[3-[[2-(3-Cycloheptyl-2-propenyl)thio]ethyl]-7-thiabicyclo[2.2.1]hept-2-yl]-5-heptenoic acid Following the procedure of Examples 4, 5, 8 and 20 except substituting 3-cycloheptyl-prop-2-ene-1-thiol for 1-hexanethiol, the title compound is obtained.

EXAMPLE 89

[1β,2α(5Z),3α,4β]-7-[3-[[4-(3-Phenyl-2-propenyl)thio]butyl]-7-thiabicyclo[2.2.1]hept-2-yl]-5-heptenoic acid Following the procedure of Examples 48, 4 and 5 except substituting the Example 26 Part C alcohol for the alcohol used in Example 4 and substituting 3-phenyl-prop-2-ene-1-thiol for 1-hexanethiol, the title compound is obtained.

EXAMPLE 90

[1β,2α(5Z),3α,4β]-7-[3-[[4-(6-Phenyl-3-hexynyl)oxy]butyl]-7-thiabicyclo[2.2.1]hept-2-yl]-5-heptenoic acid Following the procedure of Examples 26, 1 and 2 except substituting 6-phenyl-hex-3-ynyl methanesulfonate for n-hexyl methanesulfonate, the title compound is obtained.

EXAMPLE 91

[1β,2α(5Z),3α,4β]-7-[3-[[4-(7-Phenyl-3-heptenyl)thio]butyl]-7-thiabicyclo[2.2.1]hept-2-yl]-5-heptenoic acid Following the procedure of Examples 89, 4 and 5 except substituting 7-phenyl-hept-3-ene-1-thiol for 3-phenyl-prop-2-ene-1-thiol, the title compound is obtained.

EXAMPLE 92

(1β,2α,3α,4β)-7-[3-[[4-(5-Hexenyl)thio]butyl]-7-thiabicyclo[2.2.1]hept-2-yl]heptanoic acid Following the procedure of Examples 4, 5, 8 and 89 except substituting hex-5-ene-1-thiol for 3-phenyl-prop-2-ene-1-thiol, the title compound is obtained.

EXAMPLE 93

[1β,2α(5Z),3α,4β]-7-[3-[[4-(6-Heptynyl)thio]butyl]-7-thiabicyclo[2.2.1]hept-2-yl]-5-heptenoic acid Following the procedure of Examples 4, 5 and 89 except substituting hept-6-yne-1-thiol for 3-phenyl-prop-2-ene-1-thiol, the title compound is obtained.

EXAMPLES 94 TO 100

Following the procedure as set out in the preceding Examples wherein compounds wherein A is $(CH_2)_2$ or $-CH=CH$ and X is O or $S(O)_n$, are obtained except substituting for (4-carboxybutyl) triphenylphosphonium bromide in the phosphonium compound shown in Column I of the Table set out below, the compound shown in Column II is obtained.

| | Column I |
|---|---|
| | $(C_6H_5)P-CH_2-(CH_2)_n-CO_2H$ |

Column II: thiabicyclo structure with $CH_2-A-(CH_2)_n-CO_2H$ and $(CH_2)_p-X-R^1$ substituents

| Ex. No. | $(CH_2)_n$ | $(CH_2)_n$ |
|---|---|---|
| 94. | $(CH_2)_4$ | |
| 95. | | $-CH_2-CH_2-\overset{CH_3}{\underset{CH_3}{CH}}-$    As in Column I |
| 96. | | $-CH_2-CH_2-\overset{H}{\underset{CH_3}{C}}-$ |
| 97. | | $-\overset{CH_3}{CH}-CH_2-\overset{CH_3}{CH}-$ |
| 98. | $-(CH_2)_5-$ | |
| 99. | $-(CH_2)_6-$ | |
| 100. | $-CH_2-CH_2-CF_2-$ | |

It will be appreciated that following the procedure of Examples 6, 7, 52 and 53, the thiabicyclo compounds described in the above Examples may be converted into the corresponding S-oxides.

What is claimed is:

1. A compound of the structure

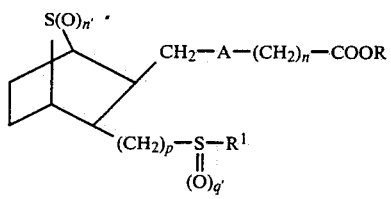

including all stereoisomers thereof, wherein A is —CH=CH— or —CH₂—CH₂—; n is 0 to 8; n' is 0 or 1; p is 1 to 4; wherein q is 0, 1 or 2; R is H, lower alkyl, alkali metal or tris(hydroxymethyl)aminomethane; and R¹ is lower alkyl, aryl, arylalkyl, cycloalkyl, cycloalkylalkyl, lower alkenyl or lower alkynyl.

2. A compound of the structure

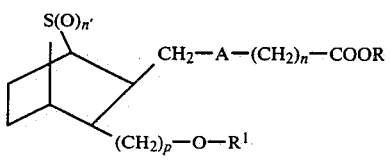

including all stereoisomers thereof, wherein A is —CH=CH— or —CH₂—CH₂—; n is 0 to 8; n' is 0 or 1; p is 1 to 4; R is H, lower alkyl, alkali metal or tris(bhydroxymethyl)aminomethane; and R¹ is lower alkyl, aryl, arylalkyl, cycloalkyl, cycloalkylalkyl, lower alkenyl or lower alkynyl.

3. The compound as defined in claim 1 wherein p is 1.

4. The compound as defined in claim 1 wherein n is 2 to 4.

5. The compound as defined in claim 1 wherein A is CH₂—CH₂ or CH=CH, p is 1, n is 2 to 4, R is H and R¹ is lower alkyl.

6. The compound as defined in claim 1 wherein R¹ is butyl, pentyl, hexyl or heptyl including all isomers thereof.

7. The compound as defined in clam 2 having the name [1β,2α(5Z),3α,4β]-7-[3-[(Hexyloxy)methyl]-7-thiabicyclo[2.2.1]hept-2-yl]-5-heptenoic acid or the hexyl ester thereof, including all stereoisomers thereof.

8. The compound as defined in claim 2 having the name [1β,2α(5Z),3α,4β]-7-[3-[(hexyloxy)methyl]-7-thiabicyclo[2.2.1]hept-2-yl]heptenoic acid, 7-oxide including all stereoisomers thereof.

9. The compound as defined in claim 1 [1β,2α(5Z),3α,4β]-7-[3-[(Hexylthio)methyl]-7-thiabicyclo[2.2.1]hept-2-yl]-5-heptenoic acid or the methyl ester thereof including all stereoisomers thereof.

10. The compound as defined in claim 2 wherein p is 1.

11. The compound as defined in claim 2 wherein n is 2 to 4.

12. The compound as defined in claim 2 wherein A is CH₂—CH₂ or CH=CH, p is 1, n is 2 to 4, R is H and R¹ is lower alkyl.

13. The compound as defined in claim 1 wherein R¹ is butyl, pentyl, hexyl or heptyl including all isomers thereof.

14. The compound as defined in claim 1 having the name [1β,2α(5Z),3α,4β]-7-[3-[(hexylthio)methyl]-7-thiabicyclo[2.2.1]hept-2-yl]-5-heptenoic acid, 7-oxide, the methyl esters thereof, including all stereoisomers thereof.

15. A method of inhibiting arachidonic acid-induced platelet aggregation and bronchoconstriction, which comprises administering to the circulatory system of a mammalian host an effective amount of a compound as defined in claim 2 or a pharmaceutically acceptable salt thereof.

16. The method as defined in claim 15 wherein said compound is administered in an amount within the range of from about 1 to about 100 mg/kg.

17. A composition for inhibiting arachidonic acid-induced platelet aggregation and bronchoconstriction comprising an effective amount of a compound as defined in claim 2 or a pharmaceutically acceptable salt thereof, and a pharmaceutically acceptable carrier therefor.

18. A method of inhibiting platelet aggregation which comprises administering to a mammalian host an effective amount of a compound as defined in claim 2 or a pharmaceutically acceptable salt thereof.

19. A method of inhibiting bronchoconstriction associated with asthma, which comprises administering to a mammalian host an effective amount of a compound as defined in claim 2 or a pharmaceutically acceptable salt thereof.

20. A method for treating peripheral vascular disease, which comprises topically or systemically administering to a mammalian host an effective amount of a compound as defined in claim 2 or a pharmaceutically acceptable salt thereof.

* * * * *